(12) United States Patent
Alvaro et al.

(10) Patent No.: US 7,534,893 B2
(45) Date of Patent: May 19, 2009

(54) IMIDAZOL-2-ONE COMPOUNDS USEFUL IN THE TREATMENT OF VARIOUS DISORDERS

(75) Inventors: Giuseppe Alvaro, Verona (IT); Damiano Ghirlanda, Verona (IT)

(73) Assignee: Glaxo Group Limited, Middlesex (GB)

( * ) Notice: Subject to any disclaimer, the term of this patent is extended or adjusted under 35 U.S.C. 154(b) by 78 days.

(21) Appl. No.: 11/570,059

(22) PCT Filed: Jun. 7, 2005

(86) PCT No.: PCT/EP2005/006183

§ 371 (c)(1),
(2), (4) Date: Dec. 5, 2006

(87) PCT Pub. No.: WO2005/121122

PCT Pub. Date: Dec. 22, 2005

(65) Prior Publication Data
US 2007/0249679 A1 Oct. 25, 2007

(30) Foreign Application Priority Data
Jun. 9, 2004 (GB) ................................ 0412865.8

(51) Int. Cl.
C07D 405/00 (2006.01)
C07D 233/00 (2006.01)
(52) U.S. Cl. .................... 546/210; 548/316.4
(58) Field of Classification Search .................. 546/219
See application file for complete search history.

(56) References Cited

U.S. PATENT DOCUMENTS

| 3,097,209 | A | 7/1963 | Janssen et al. |
| 5,567,700 | A | 10/1996 | Miller et al. |
| 5,677,317 | A | 10/1997 | Miller et al. |
| 5,780,466 | A | 7/1998 | Emonds-Alt et al. |
| 5,994,376 | A | 11/1999 | Freyne et al. |
| 6,204,265 | B1 * | 3/2001 | Reichard et al. ......... 514/235.8 |

FOREIGN PATENT DOCUMENTS

| DE | 19603787 A | 8/1997 |
| EP | 0000485 A | 2/1979 |
| WO | WO-9631465 A | 10/1996 |
| WO | WO-99 25685 A | 5/1999 |
| WO | WO-02 32666 A | 4/2002 |
| WO | WO-03 088908 A | 10/2003 |
| WO | WO-2004 005256 A | 1/2004 |
| WO | WO-2004 020411 A | 3/2004 |
| WO | WO-2004 056771 A | 7/2004 |
| WO | WO-2004 099143 A | 11/2004 |

* cited by examiner

*Primary Examiner*—D. Margaret Seaman
*Assistant Examiner*—Nizal S Chandrakumar

(74) *Attorney, Agent, or Firm*—R. Steve Thomas

(57) ABSTRACT

A compound of formula (I)

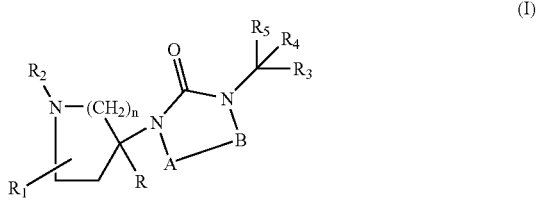

wherein:
R is a group selected from:

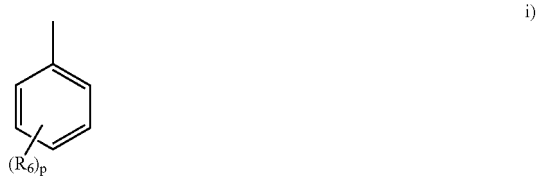

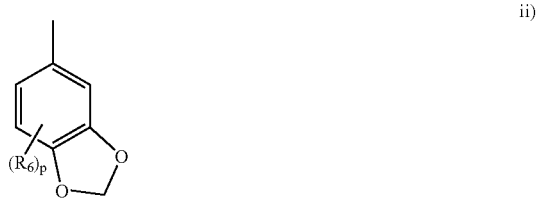

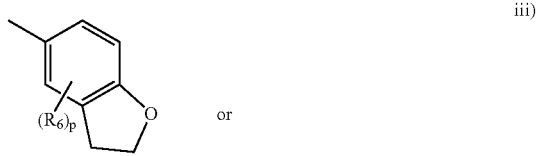

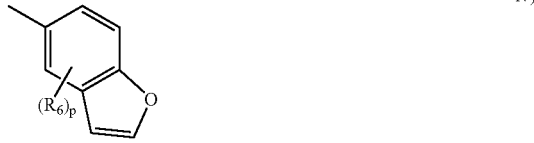

A-B is a bivalent radical of formula (v), (vi) or (vii)

$$-CH=C(R_{11})- \qquad (v)$$

$$-C(R_{10})=CH- \text{ or} \qquad (vi)$$

$$-C(R_{12})(R_{10})-C(R_{11})(R_{13})- \qquad (viii)$$

and all other variables are as defined herein or a pharmaceutically acceptable salt or solvate thereof, process for their preparation and their use in the treatment of conditions mediated by tachykinins and/or by selective inhibition of serotonin reuptake transporter protein.

10 Claims, No Drawings

IMIDAZOL-2-ONE COMPOUNDS USEFUL IN THE TREATMENT OF VARIOUS DISORDERS

This Application is filed pursuant to 35 U.S.C. §371 as a U.S. National Phase Application of International Application No. PCT/EP/2005/006183, filed 7 Jun. 2005, which claims priority to Great Britain Priority Patent Application Serial No. 0412865.8, filed 9 Jun. 2004.

The present invention relates to ureido derivatives, to processes for their preparation, to pharmaceutical compositions containing them and to their medical use.

WO 9631485 discloses compounds having general formula (A) useful for the treatment of diseases related to an abnormal enzymatic or catalytic activity of phosphodiesterase IV and diseases related to a physiological detrimental excess of cytokines.

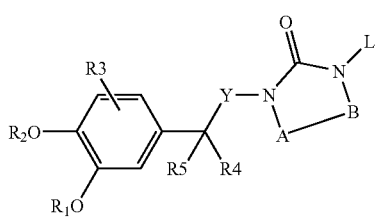

However, in the above cited document there is neither disclosure nor suggestion of any compound as claimed herein.

The present invention thus provides compounds of formula (I)

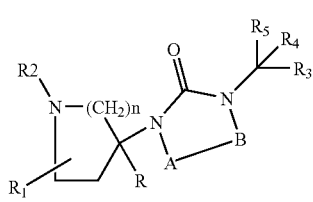

wherein:

R represents a group selected from:

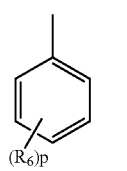

i)

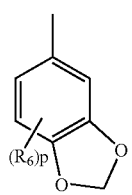

ii)

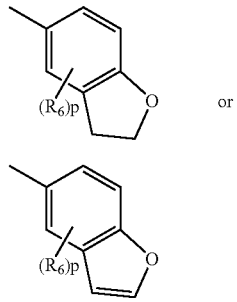

iii)

iv)

in which $R_6$ is halogen, cyano, $C_{1-4}$ alkyl or trifluoromethyl and p is 2 or 3 or $R_6$ is halogen, cyano, $C_{1-4}$ alkyl, $C_{1-4}$ alkoxy, trifluoromethoxy or trifluoromethyl and p is 0 or 1;

$R_1$ represents hydrogen, halogen, cyano, $C_{2-4}$ alkenyl, $C_{1-4}$ alkyl optionally substituted by halogen, cyano or $C_{1-4}$ alkoxy;

$R_2$ represents hydrogen or $(CH_2)qR_7$;

$R_3$ and $R_4$ each independently are hydrogen or $C_{1-4}$ alkyl;

$R_5$ represents:
  phenyl substituted by 1 to 3 groups independently selected from trifluoromethyl, $C_{1-4}$ alkyl, cyano, $C_{1-4}$ alkoxy, trifluoromethoxy, halogen, $S(O)rC_{1-4}$ alkyl or a phenyl substituted by a 5 or 6 membered heteroaryl group optionally substituted by 1 to 3 groups independently selected from trifluoromethyl, $C_{1-4}$ alkyl, cyano, $C_{1-4}$ alkoxy, trifluoromethoxy, halogen or $S(O)rC_{1-4}$ alkyl;
  naphthyl substituted by 1 to 3 groups independently selected from trifluoromethyl, $C_{1-4}$ alkyl, cyano, $C_{1-4}$ alkoxy, trifluoromethoxy, halogen or $S(O)rC_{1-4}$ alkyl;
  a 9 to 10 membered fused bicyclic heterocyclic group substituted by 1 to 3 groups independently selected from trifluoromethyl, $C_{1-4}$ alkyl, cyano, $C_{1-4}$ alkoxy, trifluoromethoxy, halogen or $S(O)rC_{1-4}$ alkyl or
  $R_5$ is a 5 or 6 membered heteroaryl group substituted by 1 to 3 groups independently selected from trifluoromethyl, $C_{1-4}$ alkyl, cyano, $C_{1-4}$ alkoxy, trifluoromethoxy, halogen or $S(O)_rC_{1-4}$alkyl;

$R_7$ is hydrogen, $C_{3-7}$ cycloalkyl, $C_{1-4}$ alkoxy, amine, $C_{1-4}$ alkylamine, $(C_{1-4}$ alkyl$)_2$amine, $OC(O)NR_8R_9$ or $C(O)NR_8R_9$;

$R_8$ and $R_9$ each independently represent hydrogen, $C_{1-4}$ alkyl or $C_{3-7}$ cycloalkyl;

A-B is a bivalent radical of formula (v), (vi) or (vii)

—CH=C($R_{11}$)—     (v)

—C($R_{10}$)=CH— or     (vi)

—C($R_{12}$)($R_{10}$)—C($R_{11}$)($R_{13}$)— wherein $R_{10}$, $R_{11}$, $R_{12}$ and $R_{13}$ each independently are hydrogen or $C_{1-4}$ alkyl;     (vii)

n is 1 or 2;
q is an integer from 1 to 4;
r is 1 or 2;

or pharmaceutically acceptable salts and solvates thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric, hydroiodic, metaphosphoric, or phosphoric acid; and organic acids e.g. succinic, maleic, acetic, fumaric, citric, tartaric, benzoic, trifluoroacetic, malic, lactic, formic, propionic, glycolic, gluconic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), ethanesulfonic, pantothenic, stearic, sulfinilic, alginic and galacturonic acid; and arylsulfonic, for example benzenesulfonic, p-toluenesulfonic, methanesulfonic or naphthalenesulfonic acid; base addition salts formed with alkali metals and alkaline earth metals and organic bases such as N,N-dibenzylethylenediamine, chloroprocaine, choline, diethanolamine, ethylenediamine, meglumine (N-methylglucamine), lysine and procaine; and internally formed salts. Certain of the compounds of formula (I) may form acid addition salts with less than one or one or more equivalents of the acid, for example to form a dihydrochloride salt. The present invention includes within its scope all possible stoichiometric and non-stoichiometric forms. Salts having a non-physiologically acceptable anion or cation are within the scope of the invention as useful intermediates for the preparation of physiologically acceptable salts and/or for use in non-therapeutic, for example, in vitro, situations.

The solvates may, for example, be hydrates.

This invention also includes within its scope stoichiometric hydrates or solvates as well as compounds containing variable amounts of water and/or solvent.

The compounds of formula (I) may be prepared in crystalline or non-crystalline form, and, if crystalline, may optionally be hydrated or solvated. Furthermore, some of the crystalline forms of the compounds of formula (I) may exist in alternative polymorphic forms, which are included in the present invention.

It will be appreciated by those skilled in the art that the compounds of formula (I), when n is 1 and when n is 2 and $R_1$ is not hydrogen, contain at least one chiral centre (namely the carbon atom shown as * in formula (I)) and may be represented by formulas (1a) and (1b).

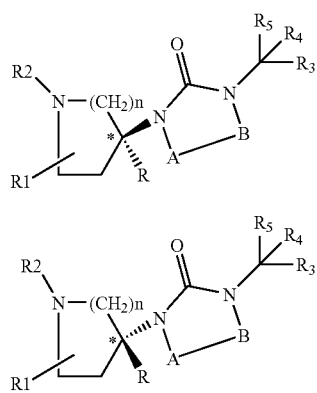

The wedged bond indicates that the bond is above the plane of the paper. The broken bond indicates that the bond is below the plane of the paper.

Further asymmetric carbon atoms are possible when $R_3$ and $R_4$ are not the same group and/or $R_1$ is different from hydrogen and/or when A-B is —C($R_{12}$)($R_{10}$)—C($R_{11}$)($R_{13}$)— in which $R_{10}$, $R_{12}$ are not the same group or and/or $R_{11}$, $R_{13}$ are not the same group.

It is to be understood that all stereoisomeric forms, including all enantiomers, diastereoisomers and all mixtures thereof, including racemates, are encompassed within the scope of the present invention and the reference to compounds of formula (I) includes all stereoisomeric forms unless otherwise stated.

Furthermore, some of the crystalline forms of the compounds of formula (I) may exist as polymorphs, which are included in the present invention.

The present invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically—labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula I and following of this invention can generally be prepared by carrying out the procedures disclosed in the Schemes and/or in the Examples below, by substituting a readily available isotopically labeled reagent for a non-isotopically labeled reagent.

The term $C_{1-4}$ alkyl as used herein as a group or a part of the group refers to a straight or branched alkyl group containing from 1 to 4 carbon atoms; examples of such groups include methyl, ethyl, propyl, iso-propyl, n-butyl, iso-butyl, tert-butyl.

The term halogen refers to fluorine, chlorine, bromine or iodine.

The term $C_{3-7}$ cycloalkyl group means a non aromatic monocyclic hydrocarbon ring of 3 to 7 carbon atoms such as, for example, cyclopropyl, cyclobutyl, cyclopentyl, cyclohexyl or cycloheptyl.

The term $C_{1-4}$ alkoxy group may be a straight chain or a branched chain alkoxy group, for example methoxy, ethoxy, prop-1-oxy, prop-2-oxy, but-1-oxy, but-2-oxy or 2-methylprop-2-oxy.

When $R_5$ is a 5 or 6 membered heteroaryl group according to the invention this includes furanyl, thiophenyl, pyrrolyl, imidazolyl, thiazolyl, oxazolyl, pyrazolyl, isoxazolyl, isothiazolyl, 1,2,3-triazolyl, 1,2,3-oxadiazolyl, 1,2,3-thiadiazolyl, 1,2,4-triazolyl, 1,3,4-oxadiazolyl, 1,3,4-thiadiazolyl, 1,2,5-oxadiazolyl, 1,2,5-thiadiazolyl, pyridyl, pyridazinyl, pyrimidinyl, pyrazinyl, 1,2,4-oxadiazolyl, 1,2,5-triazinyl or 1,3,5-triazinyl and the like.

The term 9 to 10 membered fused bicyclic heterocyclic group refers to a 5, 6/6, 5 or 6, 6 bicyclic ring system, containing at least one heteroatom selected from oxygen, sulphur or nitrogen, which may be saturated, unsaturated or aromatic. The term 9 to 10 membered fused bicyclic heterocyclic group also refers to a phenyl fused to a 5 or 6 membered heterocyclic group. Example of such groups include benzofuranyl, benzothiophenyl, indolyl, benzoxazolyl, 3H-imidazo[4,5-c]pyridin-yl, dihydrophthazinyl, 1H-imidazo[4,5-c]pyridin-1-yl, imidazo[4,5-b]pyridyl, 1,3-benzo[1,3]dioxolyl, 2H-chromanyl, isochromanyl, 5-oxo-2,3-dihydro-5H-[1,3]thiazolo[3,2-a]pyrimidyl, 1,3-benzothiazolyl, 1,4,5,6-tetrahydropyridazyl, 1,2,3,4,7,8-hexahydropteridinyl, 2-thioxo-2,3,6,9-tetrahydro-1H-purin-8-yl, 3,7-dihydro-1H-purin-8-yl, 3,4-dihydropyrimidin-1-yl, 2,3-dihydro-1,4-benzodioxinyl, benzo[1,3]dioxolyl, 2H-chromenyl, chromanyl, 3,4-dihydrophthalazinyl, 2,3-dihydro-1H-indolyl, 1,3-dihydro-2H-isoindol-2-yl, 2,4,7-trioxo-1,2,3,4,7,8-hexahydropteridinyl, thieno[3,2-d]pyrimidinyl, 4-oxo-4,7-dihydro-3H-pyrrolo[2,3-d]pyrimidinyl, 1,3-dimethyl-6-oxo-2-thioxo-2,3,6,9-tetrahydro-1H-purinyl, 1,2-dihydroisoquinolinyl, 2-oxo-1,3-benzoxazolyl, 2,3-dihydro-5H-1,3-thiazolo[3,2-a]pyrimidinyl, 5,6,7,8-tetrahydro-quinazolinyl, 4-oxochromanyl, 1,3-benzothiazolyl, benzimidazolyl, benzotriazolyl, purinyl, furylpyridyl, thiophenylpyrimidyl, thiophenylpyridyl, pyrrolylpiridyl, oxazolylpyridyl, thiazolylpiridyl, 3,4-dihydropyrimidin-1-yl imidazolylpiridyl, quinoliyl, isoquinolinyl, quinazolinyl, quinoxalinyl, naphthyridinyl, pyrazolyl[3,4]pyridine, 1,2-dihydroisoquinolinyl, cinnolinyl, 2,3-dihydro-benzo[1,4]dioxin-6-yl, 4,5,6,7-tetrahydro-benzo[b]thiophenyl-2-yl, 1,8-naphthyridinyl, 1,6-naphthyridinyl, 3,4-dihydro-2H-1,4-benzothiazine, 4,8-dihydroxy-quinolinyl, 1-oxo-1,2-dihydro-isoquinolinyl or 4-phenyl-[1,2,3]thiadiazolyl and the like.

In the compounds of formula (I), wherein n is 1, the group $R_1$ may be in position 1, 3 or 4, as represented in formula (1c).

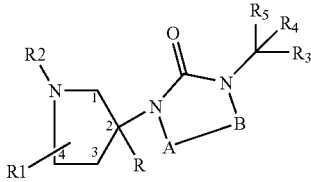

(1c)

In the compounds of formula (I), wherein n is 2, the group $R_1$ may be in position 2, 3, 5 or 6 of the piperidine ring as represented in formula (1d).

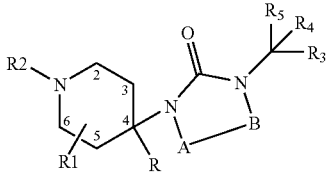

(1d)

In one embodiment n is 2.

In one embodiment R is phenyl optionally substituted by one or two halogen (e.g. fluorine) or $C_{1-4}$ alkyl (e.g. methyl).

In a further embodiment R is phenyl optionally substituted by one halogen (e.g. fluorine).

In one embodiment $R_1$ is hydrogen.

In one embodiment $R_2$ is hydrogen or $C_{1-4}$ alkyl (e.g. methyl).

In one embodiment $R_3$ is hydrogen.

In one embodiment $R_4$ is hydrogen or methyl.

In one embodiment $R_5$ is phenyl optionally substituted by one or 2 groups selected from cyano, methyl, chlorine, bromine or fluorine or $R_5$ is naphthyl optionally substituted by one group selected from cyano, methyl, chlorine, bromine or fluorine.

In a further embodiment $R_5$ is phenyl optionally substituted by one or 2 groups selected from chlorine, bromine or fluorine or $R_5$ is naphthyl optionally substituted by one group selected from cyano, chlorine, bromine or fluorine.

$R_{10}$ is preferably hydrogen or methyl.
$R_{11}$ is preferably hydrogen or methyl.
$R_{12}$ is preferably hydrogen or methyl.
$R_{13}$ is preferably hydrogen or methyl.

In one embodiment R is phenyl substituted by a fluorine, $R_1$ is hydrogen, $R_2$ is hydrogen or $C_{1-4}$ alkyl (e.g. methyl), $R_3$ is hydrogen, $R_4$ is hydrogen or methyl, $R_5$ is phenyl or naphthyl optionally substituted by one or two groups independently selected from cyano, chlorine, bromine or fluorine, $R_{10}$, $R_{11}$, $R_{12}$ or $R_{13}$ are hydrogen and n is 2.

Preferred compounds according to the invention are:

1-[(3,5-dichlorophenyl)methyl]-3-[4-(4-fluorophenyl)-1-methyl-4-piperidinyl]-1,3-dihydro-2H-imidazol-2-one;

1-[(3,5-dichlorophenyl)methyl]-3-[4-(4-fluorophenyl)-1-methyl-4-piperidinyl]-1,3-dihydro-2H-imidazol-2-one;

1-[(3,5-Dichlorophenyl)methyl]-3-[4-(4-fluorophenyl)-4-piperidinyl]-1,3-dihydro-2H-imidazol-2-one;

1-[1-(3,5-Dichlorophenyl)ethyl]-3-[4-(4-fluorophenyl)-1-methyl-4-piperidinyl]-1,3-dihydro-2H-imidazol-2-one;

1-[1-(3-Chloro-1-naphthalenyl)ethyl]-3-[4-(4-fluorophenyl)-1-methyl-4-piperidinyl]-1,3-dihydro-2H-imidazol-2-one;

1-[1-(3,5-Dichlorophenyl)ethyl]-3-[4-(4-fluorophenyl)-1-methyl-4-piperidinyl]-1,3-dihydro-2H-imidazol-2-one;

1-[1-(3-Chloro-1-naphthalenyl)ethyl]-3-[4-(4-fluorophenyl)-1-methyl-4-piperidinyl]-1,3-dihydro-2H-imidazol-2-one;

1-[(3,5-dichlorophenyl)methyl]-3-[4-(4-fluorophenyl)-1-methyl-4-piperidinyl]-2-imidazolidinone;

4-({3-[4-(4-fluorophenyl)-1-methyl-4-piperidinyl]-2-oxo-1-imidazolidinyl}methyl)-2-naphthalenecarbonitrile;

7-fluoro-4-({3-[4-(4-fluorophenyl)-1-methyl-4-piperidinyl]-2-oxo-1-imidazolidinyl}methyl)-2-naphthalenecarbonitrile;

6-fluoro-4-({3-[4-(4-fluorophenyl)-1-methyl-4-piperidinyl]-2-oxo-1-imidazolidinyl}methyl)-2-naphthalenecarbonitrile;

1-[(3-chloro-1-naphthalenyl)methyl]-3-[4-(4-fluorophenyl)-1-methyl-4-piperidinyl]-1,3-dihydro-2H-imidazol-2-one;

and enantiomers, diastereoisomers, phamaceutically acceptable salts (e.g hydrochloride, fumarate or citrate) and solvates thereof.

The compounds of the invention are antagonists of tachykinin receptors, including substance P and other neurokinins, both in vitro and in vivo and are thus of use in the treatment of conditions mediated by tachykinins, including substance P and other neurokinins.

Tachykinins are a family of peptides that share a common carboxyl-terminal sequence (Phe-X-Gly-Leu-Met-NH2). They are actively involved in the physiology of both lower and advanced lifeforms. In mammalian lifeforms the main tachykinins are substance P (SP), Neurokinin A (NKA) and Neurokinin B (NKB) which act as neurotransmitters and neuromodulators. Mammalian tachykinins may contribute to the pathophysiology of a number of human diseases.

Three types of tachykinins receptors have been identified, namely NK1 (SP-preferring), NK2 (NKA-preferring) and NK3 (NKB-preferring) which are widely distributed throughout the central nervous (CNS) and peripheral nervous system.

Particularly the compounds of the invention are antagonists of the NK1 receptor.

The compounds of the present invention also have activity as selective serotonin reuptake inhibitors (hereinafter referred to as SSRIs) and are thus of use in the treatment of conditions mediated by selective inhibition of the serotonin reuptake transporter protein.

Thus, the compounds of the present invention combine dual activity as tachykinin antagonists, including substance P and other neurokinins, and as SSRIs. In particular, the compounds of the invention combine dual activity as NK1 receptor antagonists and as SSRIs.

$NK_1$ receptor binding affinity has been determined in vitro in a binding Scintillation proximity assay (SPA) by measuring the compounds' ability to displace [$^{125}$I]Tyr8-Substance P (SP) from recombinant human $NK_1$ receptors stably expressed in Chinese Hamster Ovary (CHO) cell membranes prepared by using a modification of the method described by Beattie D. T. et al. (Br. J. Pharmacol, 116:3149-3157, 1995). Briefly, polystrene Leadseeker WGA-SPA beads (Amersham Biosciences) were mixed with cell membranes in a bead/membrane ratio of 50:1 (w/w) in assay buffer (75 mM Tris pH 7.8, 75 mM NaCl, 4 mM MnCl2, 1 mM EDTA, 0.05% Chaps, 1 mM PMSF). The mixture was placed on ice for 30 minutes to allow the formation of membrane/bead complex before BSA was added to a final concentration of 1%. After another 30 minutes incubation on ice, the bead/membrane complex washed twice and suspended in assay buffer. [$^{125}$I]Tyr8-SP (2200 Ci/mmol, PerkinElmer) was then added to the bead/membrane complex with a final concentration of 0.4 nM. 30 ul of the resulting mixture was then dispensed to each well of Nalgen NUNC 384-well plate with 1 ul compound pre-dispensed in DMSO. The plates were then sealed and pulse centrifuged at 1100 rpm. After 3 hours incubation at room temperature with shaking, the plates were centrifuged for 2 min at 1100 rpm and measured in Viewlux imager (PerkinElmer) for 5 minutes with a 618-nm filter. Inhibition of [$^{125}$I]Tyr8-SP binding to $NK_1$ receptors was measured by the reduction of luminescent signal. $IC_{50}$ values of each compound were determined by an 11-point 3×-dilution inhibition curve. $pK_i$ values were calculated using the $K_D$ of [$^{125}$I]Tyr8-SP determined in a separate experiment.

For representative compounds of the invention $NK_1$-receptor binding affinity has also been determined in vitro using conventional filtration techniques by measuring the compounds' ability to displace [$^3$H]-SP from recombinant human $NK_1$ receptors expressed in CHO cell membranes prepared as described above. Briefly, ligand binding was performed in 0.2 ml of 50 mM HEPES, pH 7.4, containing 3 mM $MnCl_2$, 0.02% BSA, 0.5 nM [$^3$H]-SP (30-56 Ci/mmol Amersham), a final membrane protein concentration of 30-50 µg/ml, and the test compounds. The incubation proceeded at room temperature for 40 min and was stopped by filtration. Non-specific binding was determined using excess of SP (1 µM) and represents about 6-10% of the total binding.

Compounds of the invention were further characterised in a functional assay using FLIPR technology for the determination of their effect to inhibit the intracellular calcium increase induced by SP in both Human-$NK_1$—CHO cells and human U2OS cells transducted with $NK_1$ BacMan virus. Briefly, 10K-15K cells/well were seeded in 384 well Greiner bio-one plate in culture medium (DMEM with 10% FBS), incubated overnight in CO2 at 37° C. For human U2OS cells, 1% (v/v) BacMan virus carrying $NK_1$ gene was mixed with cells before plating. After aspirating the medium, cells were loaded with cytoplasmic calcium indicator Calcium 3 dye (Molecular Devices Co.) in 30 ul/well buffer (Hank's balanced salts with 20 mM Hepes) and incubated in CO2 at 37° C. for 60 minutes. 10 ul/well assay buffer buffer (Hank's balanced salts with 20 mM Hepes) containing different concentrations of compounds was then added to the cells for another 30 minutes incubation at 37° C. Finally, 10 ul/well SP in assay buffer containing 0.1% BSA was added to the cells and fluorescence signal read on a FLIPR system. $pIC_{50}$ values of each compound were determined by an 11-point 3×-dilution inhibition curve. The potency of the antagonist ($fpK_i$ value or $pK_B$ value) was calculated from $pIC_{50}$ by the Cheng-Prusoff equation or calculated from Schild's analysis.

Human serotonin transporter (hSERT) binding affinity has been determined in vitro by the compounds' ability to displace [$^3$H]-citalopram from membranes derived from porcine LLCPK cells (ATCC.) stably transfected with the hSERT (hSERT-LLCPK). For the binding reaction, a final concentration of 0.25 nM of [$^3$H]-citalopram (84 Ci/mmol, Amersham) were incubated with 3-5 µg/ml of cell membrane and the compound to be tested in 50 mM Tris HCl, pH 7.7, containing 120 mM NaCl, 5 mM KCl, 10 µM pargyline and 0.1% ascorbic acid. The reaction was performed for 120 min at 22° C. and was terminated through GF/B Unifilter (pre-soaked in 0.5% PEI) using a Cell Harvester. Scintillation fluid was added to each filtered spot and radioactivity was determined using a scintillation counter (TopCount (Packard)). Non-specific binding was determined using paroxetine (10 µM) and represents about 2-5% of the total binding. Competition experiments were conducted with duplicate determination for each point. $pIC_{50}$ values of each compound were determined by an 7-point 2×-dilution inhibition curve. The affinity of the inhibitor ($pK_i$ value) was calculated from $pIC_{50}$ by the Cheng-Prusoff equation and by using the $K_D$ of [$^3$H]-citalopram determined in separate experiments.

For representative compounds of the invention, the inhibitory activity of the compounds at the hSERT has been determined in vitro using hSERT-LLCPK cells. The cells have been plated onto 96-well plates (10000 cells/well). After 24 hr, cells have been washed in uptake buffer (Hank's balanced salt solution+20 mM Hepes) and pre-incubated for 10 minutes at 30° C. with 50 µl of buffer containing the test compounds. 50 µl of 50 nM [$^3$H]Serotonin (5-HT) solution (final concentration: 25 nM [$^3$H] 5-HT) have been added and plates have been incubated for 7 min at 30° C., during which cells take up radiolabelled 5-HT. Aspirating the solution and rapidly washing the cells with cold buffer has terminated the uptake. The amount of radioactive 5-HT incorporated in the cells has then been measured by adding the scintillation cocktail directly onto the cells and reading the plate in the Top Count. $pIC_{50}$ values of each compound were determined by an 7-point 2×-dilution inhibition curve.

The action of the compounds of the invention at the $NK_1$ receptor and/or serotonin transporter may be determined by using conventional animal models.

The anti-anxiety activity obtained by the administration of a compound according to the invention can be demonstrated in the gerbil social interaction model, according to the method described by Cheeta et al. (Cheeta S. et al., 2001. Brain Research 915: 170-175).

Compounds of the invention are useful in the treatment of CNS disorders and psychotic disorders, in particular in the treatment or prevention of depressive states and/or in the treatment of anxiety as defined in, but not restricted to, Diagnostic Statistical of Mental Disorder (DSM) IV edition edit by American Psychiatric Association and/or International Classification Diseases 10th revision (ICD-10)). The various subtypes of the disorders mentioned herein are contemplated as part of the present invention. Numbers in brackets after the listed diseases below refer to the classification code in DSM-IV.

Within the context of the present invention, the term psychotic disorder includes Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9): Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90).

Anxiety disorders including Social Anxiety Disorder, Panic Attack, Agoraphobia, Panic Disorder, Agoraphobia Without History of Panic Disorder (300.22), Specific Phobia (300.29) including the subtypes Animal Type, Natural Environment Type, Blood-Injection-Injury Type, Situational Type and Other Type), Social Phobia (300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder and Anxiety Disorder Not Otherwise Specified (300.00):

Compounds of the invention are also useful in the treatment of Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition; and Substance-Induced Sleep Disorder including the subtypes Insomnia Type, Hypersomnia Type, Parasomnia Type and Mixed Type.

Compounds of the invention may be also useful in the treatment of Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-induced Persisting Amnestic Disorder, Substance-Induced Psychotic Disorder, Substance-induced Mood Disorder, Substance-Induced Anxiety Disorder, Substance-induced Sexual Dysfunction, Substance-induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-induced Persisting Amnestic Disorder, Alcohol-induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-induced Psychotic Disorder, Hallucinogen-induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid- Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Compounds of the invention may be also useful in the treatment of Autistic Disorder (299.00); Attention-Deficit/ Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

Compounds of the invention may be also useful in the treatment of Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9).

Compounds of the invention may be also useful in the treatment of eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; and Eating Disorder Not Otherwise Specified (307.50).

The compounds of the invention may be also useful in the treatment Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

Compounds of the invention may be useful as analgesics. In particular, they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch and thalamic pain such as post stroke thalamic pain.

Compounds of the invention may be also useful in the treatment or prevention of the cognitive disorders. Cognitive disorders include dementia, amnestic disorders and cognitive disorders not otherwise specified.

Furthermore, compounds of the invention may be also useful as memory and/or cognition enhancers in healthy humans with no cognitive and/or memory deficit. Enhancement of memory and/or cognition including the treatment of memory and/or cognition impairment in other diseases such as schizophrenia, bipolar disorder, depression, other psychiatric disorders and psychotic conditions associated with cognitive impairment, e.g. Alzheimer's disease.

Compounds of the invention may be also useful as anti-inflammatory agents. In particular, they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence and dental inflammation.

Compounds of the invention may be also useful in the treatment of overactive bladder disorders including symptoms of urinary frequency, with or without urge incontinence, nocturia and urgency.

Compounds of the invention may be also useful in the treatment of allergic disorders, in particular allergic disorders of the skin such as urticaria, and allergic disorders of the airways such as rhinitis.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease (GERD) such as erosive GERD and symptomatic GERD or non erosive GERD, acid indigestion, over-indulgence of food or drink, acid stomach, sour stomach, waterbrash/regurgitation, heartburn, such as episodic heartburn, nocturnal heartburn, and meal-induced heartburn, dyspepsia and functional dyspepsia.

Compounds of the invention are also useful in the treatment of gastrointestinal disorders such as irritable bowel syndrome, gastro-oesophageal reflux disease (GERD) such as erosive GERD and symptomatic GERD or non erosive GERD, acid indigestion, over-indulgence of food or drink, acid stomach, sour stomach, waterbrash/regurgitation, heartburn, such as episodic heartburn, nocturnal heartburn, and meal-induced heartburn, dyspepsia and functional dyspepsia (such as ulcer-like dyspepsia, dysmotility-like dyspepsia and unspecified dyspepsia) chronic constipation; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

The compounds of the invention may be also useful in premenstrual dysphoric disorder (PMDD), in chronic fatigue syndrome and Multiple sclerosis.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by tachykinins (including substance P and other neurokinins) and/or by selective inhibition of serotonin reuptake.

There is also provided as a further aspect of the invention the use of a compound of formula (I) or a pharmaceutically acceptable salt or solvate thereof in the treatment of conditions mediated by tachykinins (including substance P and other neurokinins) and/or by selective inhibition of the serotonin reuptake transporter protein.

In a further aspect there is provided the use of a compound of formula (I) or a pharmaceutically acceptable salt or solvate thereof in the preparation of a medicament for use in the treatment of depression and/or anxiety.

In a further aspect there is provided the use of a compound of formula (I) or a pharmaceutically acceptable salt or solvate thereof in the use in the treatment of depression and/or anxiety.

In an alternative or further aspect there is provided a method for the treatment of a mammal, including man, in particular in the treatment of conditions mediated by tachykinins, including substance P and other neurokinins, and/or by selective inhibition of the serotonin reuptake transporter protein comprising administration of an effective amount of a compound of formula (I) or a pharmaceutically acceptable salt thereof.

In a further aspect of the present invention there is provided a method for the treatment of a mammal, including man, in particular in the treatment of depression and/or anxiety which method comprises administration of an effective amount of a compound of formula (I) or a pharmaceutically acceptable salt or solvate thereof.

It will be appreciated that reference to treatment is intended to include prophylaxis as well as the alleviation of established symptoms.

Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus, compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

Thus, for parenteral administration a daily dose will typically be in the range of 1 to about 100 mg, preferably 1 to 80 mg per day. For oral administration a daily dose will typically be within the range 1 to 300 mg e.g. 1 to 100 mg.

Compounds of formula (I), and salts and solvates thereof, may be prepared by the general methods outlined hereinafter. In the following description, the groups R, $R_1$, $R_2$, $R_3$, $R_4$, $R_5$, $R_6$, $R_7$, $R_8$, $R_9$, $R_{10}$, $R_{11}$, $R_{12}$, $R_{13}$, n, p, q and r have the meaning as previously defined for compounds of formula (I) unless otherwise stated.

Compounds of formula (I), wherein A-B is —C($R_{12}$)($R_{10}$)—C($R_{11}$)($R_{13}$)—, may be prepared by N-alkylation of a compound of formula (II),

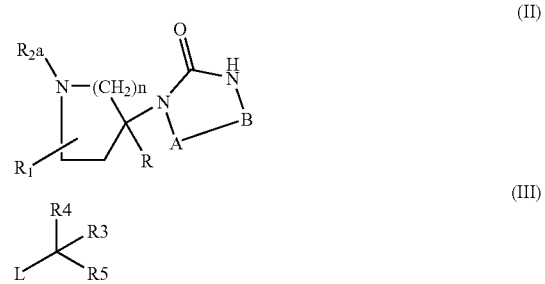

wherein $R_{2a}$ has the meaning defined in formula (I) or is a nitrogen protecting group and A-B is —C($R_{12}$)($R_{10}$)—C($R_{11}$)($R_{13}$)—, with the compound (III) wherein L is a suitable leaving group selected from halogen, mesylate or tosylate and where necessary followed by removal of the nitrogen protecting group.

The N-alkylation may be carried out in an aprotic solvent such as dichloroethane, tetrahydrofuran, N,N-dimethylformamide or acetonitrile and in the presence of a suitable base (e.g sodium hydride), preferably at a temperature ranging from 0 to 25° C.

Compounds of formula (II) may be prepared by cyclisation reaction of a compound of formula (IV),

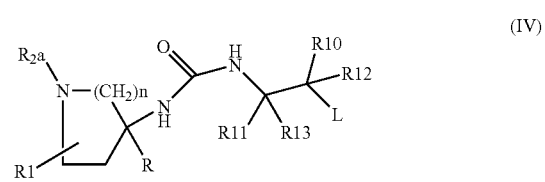

wherein $R_{2a}$ has the meaning defined in formula (II) and L is a suitable leaving group selected from halogen, mesylate or tosylate, in the presence of a base, e.g. sodium hydride.

The cyclisation reaction may be carried out in an aprotic solvent such as dichloroethane, tetrahydrofuran, N,N-dimethylformamide or acetonitrile and in the presence of a suitable base (e.g sodium hydride), preferably at a temperature ranging from 0 to 25° C.

Compounds of formula (IV) may be prepared by reaction of a compound of formula (V),

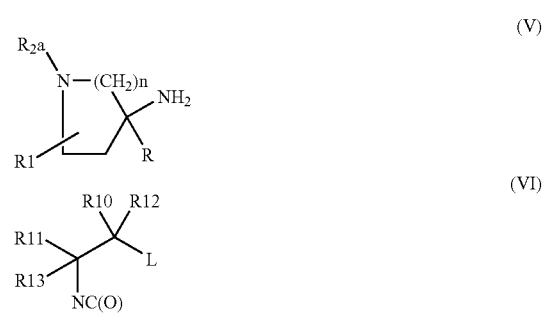

wherein $R_{2a}$ has the meaning defined in formula (II), with an isocyanate of formula (VI) wherein L is a suitable leaving group selected from halogen, mesylate or tosylate.

The reaction may be carried out in an aprotic solvent such as dichloroethane, tetrahydrofuran, N,N-dimethylformamide or acetonitrile and in the presence of a suitable base (e.g sodium hydride), preferably at a temperature ranging from 0 to 25° C.

Compounds of formula (V) may be prepared by hydrolysis of a compound of formula (VII), wherein $R_{2a}$ has the meaning defined in formula (II), in the presence of a suitable inorganic acid (e.g HCl) or base (e.g KOH).

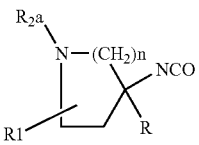

(VII)

The reaction may be carried out in an aqueous medium at a temperature ranging from 0 to reflux.

Compounds of formula (VII) may be prepared by reaction of a carboxylic acid of formula (VIII), wherein $R_{2a}$ has the meaning defined in formula (II)

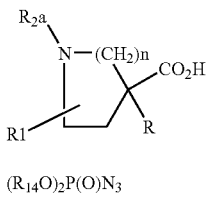

(VIII)

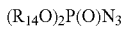

(IX)

with an azide derivative (IX) wherein $R_{14}$ is phenyl.

The reaction may be carried out in an aprotic solvent such as dichloroethane, tetrahydrofuran, N,N-dimethylformamide, toluene or acetonitrile and, preferably by heating up to the boiling point of the solvent.

Alternatively, isocyanates (VII) may be prepared by reaction of an activated derivative of the carboxylic acid (VIII) with sodium azide.

Suitable activated derivatives of the carboxyl group include the acyl halide, mixed anhydride, activated ester such as thioester or the derivative formed between the carboxylic acid group and a coupling agent such as that used in peptide chemistry, for example carbonyl diimidazole or dicyclohexylcarbodiimide.

The reaction is preferably carried out in an aprotic solvent such as hydrocarbon, halohydrocarbon such as dichloromethane or an ether such as tetrahydrofuran.

The activated derivatives of the carboxylic acid (VIII) may be prepared by conventional means.

The reaction is suitably carried out in a solvent such as N,N-dimethylformamide.

Compounds of formula (I), wherein A-B is —CH=CR$_{11}$—, may be prepared by cyclisation of a compound of formula (X), wherein $R_{2a}$ has the meaning defined in formula (II),

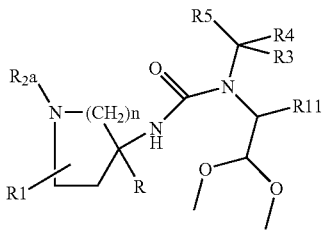

(X)

in the presence of an inorganic acid (e.g aqueous hydrochloric acid) and followed where necessary by removal of the nitrogen protecting group.

The cyclisation reaction is conveniently carried out in a solvent such as an alkanol, e.g. methanol or ethanol, at a temperature within the range 20° to 60° C.

Compounds of formula (X) may be prepared by reaction of a compound of formula (VII), wherein $R_{2a}$ has the meaning defined in formula (II), (VII)

(XI)

with an amine of formula (XI). The reaction may be carried out in an aprotic solvent such as dichloroethane, tetrahydrofuran, N,N-dimethylformamide, toluene or acetonitrile and, preferably by heating up to the boiling point of the solvent.

Compounds of formula (I), wherein A-B is —CR$_{10}$=CH—, may be prepared by cyclisation of a compound of formula (XII), wherein $R_{2a}$ has the meaning defined in formula (II), (XII)

in the presence of an inorganic acid (e.g aqueous hydrochloric acid) and followed, where necessary, by removal of the nitrogen protecting group.

The cyclisation reaction is conveniently carried out in a solvent such as an alkanol, e.g. methanol or ethanol, at a temperature within the range 20° to 60° C.

Compounds of formula (XII) may be prepared by reaction of a compound of formula (XIII) with an isocyanate (XVI)

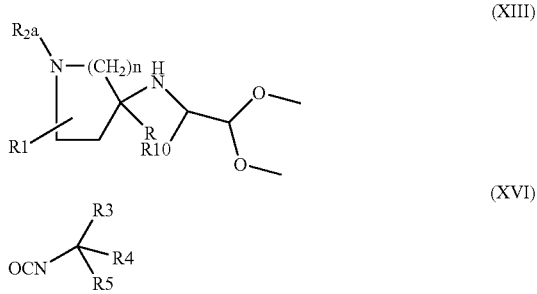

The reaction may be carried out in an aprotic solvent such as dichloroethane, tetrahydrofuran, N,N-dimethylformamide or acetonitrile and in the presence of a suitable base (e.g sodium hydride), preferably at a temperature ranging from 0 to 25° C.

Compounds of formula (XIII) may be prepared by N-alkylation of a compound of formula (V) with (XV)

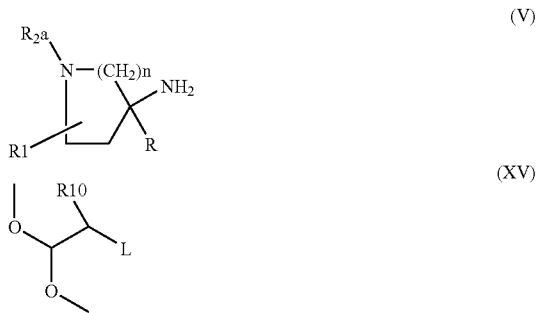

wherein L is a suitable leaving group selected from halogen, mesylate, tosylate.

The reaction may be carried out in an aprotic solvent such as dichloroethane, tetrahydrofuran, N,N-dimethylformamide or acetonitrile and in the presence of a suitable base (e.g sodium hydride), preferably at a temperature ranging from 0° C. to reflux.

Compounds of formula (XI) may be prepared by alkylation of the amine (XVI), with (XVII)

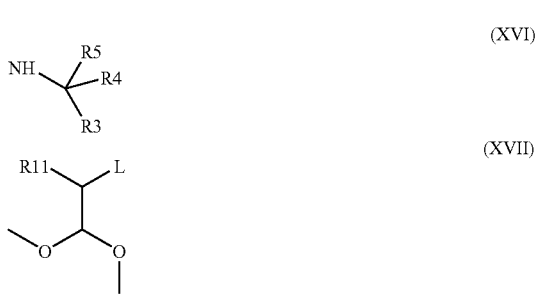

wherein L is a suitable leaving group selected from halogen, mesylate, tosylate.

The reaction may be carried out in an aprotic solvent such as dichloroethane, tetrahydrofuran, N,N-dimethylformamide or acetonitrile and in the presence of a suitable base (e.g sodium hydride), preferably at a temperature ranging from 0° C. to reflux.

Compounds of formula (I), wherein $R_2$ is hydrogen, may be also prepared by dealkylation reaction of a compound of formula (I) wherein $R_2$ is $C_{1-4}$ alkyl, with 1-chloroethyl chloridocarbonate.

The reaction is preferably carried out in an aprotic solvent such as dichloroethane, preferably at a temperature ranging from 0° C. to reflux.

When $R_{2a}$ is a nitrogen protecting group, examples of suitable groups include benzyl alkoxycarbonyl, e.g. t-butoxycarbonyl, benzyloxycarbonyl, arylsulphonyl, e.g. phenysulphonyl or 2-trimethylsilylethoxymethyl.

Protection and deprotection may be effected using conventional techniques such as those described in "Protective Groups in Organic Synthesis $3^{rd}$ Ed." by T. W. Greene and P. G. M. Wuts (John Wiley and Sons, 1999) and as described in the examples hereinafter.

Acids of formula (VIII) may be prepared according to the procedure described in WO 200422539. Compounds of formulae (III), (VI), (IX), (XV), (XVI) or (XVII) are commercially available compounds or may be prepared by analogous methods to those used for known compounds.

When a specific enantiomer or a diastereoisomer of a compound of general formula (I) is required, this may be obtained for example by resolution of a corresponding enantiomeric or a diastereoisomeric mixture of a compound of formula (I) using conventional methods. Thus, for example, specific enantiomers of the compounds of formula (I) may be obtained from the corresponding enantiomeric mixture of a compound of formula (I) using chiral HPLC procedure.

Alternatively, enantiomers of a compound of general formula (I) may be synthesised from the appropriate optically active intermediates using any of the general processes described herein.

Thus, in one embodiment of the invention the enantiomers of the compound of formula (I) may be prepared by reaction of a chiral amine (XVI) using any of the processes described above for preparing compounds of formula (I) from amine (XVI).

The chiral amine (XVI) may be prepared from the corresponding racemic amine (XVI) using any conventional procedures, such as salt formation with a suitable optically active acid such as for example di-p-toluoyl-D-tartaric acid, (S)-methoxyphenylacetic acid or di-p-toluoyl-L-tartaric acid, or using chiral HPLC procedure.

Where it is desired to isolate a compound of formula (I) as a salt, for example a pharmaceutically acceptable salt, this may be achieved by reacting a compound of formula (I) in the form of the free base with an appropriate amount of suitable acid and in a suitable solvent such as an alcohol (e.g. ethanol or methanol), an ester (e.g. ethyl acetate) or an ether (e.g. diethyl ether, tert-butylmethyl ether or tetrahydrofuran).

Biology Data

The affinity of the compound of the invention for the $NK_1$ receptor was determined using the $NK_1$ receptor binding affinity method (Scintillation proximity assay (SPA)) measured in vitro by the compounds' ability to displace [$^{125}I$] Tyr8-Substance P (SP) from recombinant human $NK_1$ receptors expressed in Chinese Hamster Ovary (CHO) cell membranes. The affinity values are expressed as negative logarithm of the inhibition constant ($pK_i$) of displacer ligands. The $pK_i$ values obtained as the average of at least two determinations with representative compounds of the invention are within the range of 7 to 9.

The affinity of the compounds of the invention for the serotonin transporter was determined using the hSERT binding affinity method and measuring in vitro the compounds' ability to displace [³H]-citalopram from recombinant human serotonin transporter expressed in Porcine Epithelial Kidney LLCPK cell membranes. The affinity values are expressed as negative logarithm of the inhibition constant of displacer ligands ($pK_i$). The $pK_i$ values obtained as the average of at least two determinations with representative compounds of the invention are within the range of 7.5 to 8.5.

PHARMACY EXAMPLES

Tablets

Tablets may be prepared by the normal method such as direct compression or wet granulation.

The tablets may be film coated with a suitable film forming material such for example Opadry using standard technique.

Example A

Tablets (Direct Compression)/Capsules

| | |
|---|---|
| Active ingredient | 20.0 mg |
| Dibasic Calcium Phospate | 123.253 mg |
| Crospovidone | 4.5 mg |
| Magnesium Stearate | 1.5 mg |
| Colloidal Silicon Dioxide | 0.75 mg |

The active ingredient is blended with the other excipients. The blend can be used to fill gelatin capsules or compressed to form tablets using appropriate punches. The tablets can be coated using conventional techniques and coatings.

Example B

Tablets/Capsules (Wet Granulation)

| | |
|---|---|
| Active ingredient | 20.0 mg |
| PVP | 3 mg |
| Avicel | 120.25 mg |
| Crospovidone | 4.5 mg |
| Magnesium Stearate | 1.5 mg |
| Colloidal Silicon Dioxide | 0.75 mg |

The Active ingredient and the intragranular excipients (PVP, Avicel, Crospovidone) are mixed at high main agitator (impeller) for a few minutes. The resulting mixture are wetted, adding the liquid binder (water) by spraying it into the powder while both agitators, impeller and chopper, are running at a low speed. The particles are let growing as resulting from the mechanical energy supplied (both agitators running at high speed) and dried by granulator chamber walls warming. The granules thus obtained are sieved and the other extragranular excipients (Magnesium Stearate, Colloidal Silicon Dioxide) are added and then mixed. The resulting mixture is compressed to obtained tablets or encapsulated to obtain capsules.

Example C

Tablets/Capsules (Dry Granulation)

| | |
|---|---|
| Active ingredient | 20.0 mg |
| PVP | 2 mg |
| Avicel | 121 mg |
| Crospovidone XL | 4.5 mg |
| Magnesium Stearate | 1.5 mg |
| Colloidal Silicon Dioxide | 1 mg |

The Active ingredient and the intragranular excipients (PVP, Avicel, Crospovidone) are mixed and the mixture is compated by compression with flat faced punches or by passing through two grooved rollers revolving toward each other, in order to obtain the "slugs" The other extragranular excipients (Magnesium Stearate, Colloidal Silicon Dioxide) are added and then mixed. The resulting mixture is compressed to obtained tablets or encapsulated to obtain capsules.

Example D

| Infusion | | |
|---|---|---|
| Active ingredient | 2-50 | mg/m Buffer |
| solution pH 4.5 suitable for infusion (e.g. sodium chloride in NaCl 0.9% or 5% dextrose) | qs to 100 ml | |

The formulation may be packed in glass vials or plastic bag.

In the Intermediates and Examples unless otherwise stated:

Melting points (m.p.) were determined on a Buchi m.p. apparatus and are uncorrected. rt refers to room temperature. Infrared spectra (IR) were measured in chloroform or nujol solutions on a FT-IR instrument. Proton Magnetic Resonance (NMR) spectra were recorded on Varian instruments at 300, 400 or 500 MHz, on Bruker instrument at 300 MHz, chemical shifts are reported in ppm (δ) using the residual solvent line as internal standard. Splitting patterns are designed as s, singlet; d, doublet; t, triplet; q, quartet; m, multiplet; b, broad. The NMR spectra were recorded at temperature ranging from 25 to 90° C.; when more than one conformer was detected the chemical shifts for the most abundant one is reported. Mass spectra (MS) were taken on a 4 II triple quadrupole Mass Spectrometer (Micromass UK) or on a Agilent MSD 1100 Mass Spectrometer, operating in ES (+) and ES (−) ionization mode or on a Agilent LC/MSD 1100 Mass Spectrometer, operating in ES (+) and ES (−) ionization mode coupled with HPLC instrument Agilent 1100 Series [LC/MS-ES (+): analysis performed on a Supelcosil ABZ+Plus (33×4.6 mm, 3 μm) (mobile phase: 100% [water+0.1% $HCO_2H$] for 1 min, then from 100% [water+0.1% $HCO_2H$] to 5% [water+0.1% $HCO_2H$] and 95% [$CH_3CN$] in 5 min, finally under these conditions for 2 min; T=40° C.; flux=1 mL/min; LC/MS-ES (−): analysis performed on a Supelcosil ABZ+Plus (33×4.6 mm, 3 μm) (mobile phase: 100% [water+0.05% $NH_3$] for 1 min, then from 100% [water+0.05% $NH_3$ to 5% [water+0.05% $NH_3$] and 95% [$CH_3CN$] in 5 min, finally under these conditions for 2 min; T=40° C.; flux=1 mL/min]. In the mass spectra only one peak in the molecular ion cluster is reported. Optical rotations were determined at 20° C. with a Jasco DIP360 instrument (l=10 cm, cell volume=1 mL, λ=589 nm).

Flash silica gel chromatography was carried out over silica gel 230-400 mesh supplied by Merck AG Darmstadt, Germany or over Varian Mega Be—Si pre-packed cartridges or over pre-packed Biotage silica cartridges.

HPLC (walk-up) refers to HPLC analysis performed on a Luna C18 (mobile phase: from 100% [water+0.05% TFA] to 5% [water+0.05% TFA] and 95% [CH$_3$CN+TFA 0.05%] in 8 min; T=40° C.; flux=1 mL/min).

T.l.c. refers to thin layer chromatography on 0.25 mm silica gel plates (60F-254 Merck) and visualized with UV light. For phase separations performed by using microfiltration devices: phase separation cartridge with polypropylene frit by Whatman or Alltech. SCX means: SCX-cartridges (loading 0.75 mmol\g) by Varian.

Solutions were dried over anhydrous sodium sulphate.

Methylene chloride was redistilled over calcium hydride and tetrahydrofuran was redistilled over sodium.

The following abbreviations are used in the text: AcOEt=ethyl acetate, DCE=dichloroethane; CH=cyclohexane, DCM=methylene chloride, DIPEA=N,N-diisopropylethylamine, DMF=N,N'-dimethylformamide, Et2O=diethyl ether, EtOH=ethanol, MeOH=methanol, TEA=triethylamine, THF=tetrahydrofuran, TFA=trifluoroacetic acid, CH3CN=acetonitrile, TBTU=O-(benzotriazol-1-yl)-N,N,N'N'-tetramethyluronium tetrafluoroborate, std=saturated.

Enantiomer 1 or enantiomer 2 means a compound of the invention or an intermediate thereof as a single enantiomer whose configuration was not determined.

Intermediate 1

[1-(3-Chloro-1-naphthalenyl)ethyl]amine

A solution of 3-chloro-naphthalenecarbaldehyde (1.93 g) in dry THF (12 mL) was added dropwise to lithium bis(trimethylsilyl)-amide 1M solution in THF (10.1 mL) at −30° C. under a Nitrogen atmosphere. The resulting yellow mixture was stirred under a Nitrogen atmosphere from −30° C. to −5° C. for 1 h, then it was cooled down to −60° C. and methyllithium 1.6M solution in Et2O (11 mL) was added keeping the internal temperature of the reaction mixture <−55° C. The resulting dark violet reaction mixture was stirred for 40 minutes at −50° C. under a Nitrogen atmosphere, then it was carefully quenched at −50° C. with aqueous 2M HCl (30 mL) until pH=2. The reaction was concentrated in vacuo and the aqueous residue washed with 1:1 CH/Et2O (50 mL). The separated aqueous phase was then made basic (pH=14) at 0° C. with NaOH pellets. This basic aqueous phase was extracted with Et2O (3×60 mL), the collected organic layers were dried and concentrated in vacuo to give the title compound (1.12 g) as a yellow oil.

T.l.c.: AcOEt/MeOH 8:2, Rf=0.25 (detection with ninhydrine).

NMR (d$_6$-DMSO): δ (ppm) 8.14 (dd, 1H); 7.94-7.85 (m, 2H); 7.73 (d, 1H); 7.58-7.50 (m, 2H); 4.80 (q, 1H); 1.35 (d, 3H).

MS (ES/+): m/z=189 [M-NH$_2$]$^+$.

Intermediate 2 and Intermediate 3

[1-(3-Chloro-1-naphthalenyl)ethyl]amine (Enantiomer 2) and [1-(3-chloro-1-naphthalenyl)ethyl] amine (Enantiomer 1)

To a solution of intermediate 1 (1.12 g) in acetone (10 mL), a solution of (S)-methoxyphenylacetic acid (0.9 g) in acetone (10 mL) was added. The thick suspension was heated at 56° C. for 40 minutes then it was stirred at rt overnight. The slurry was filtered and the solid residue washed with acetone (10 mL). The solid (0.87 g) was triturated in acetone (10 mL) by heating to reflux for 1 h, cooling to rt and stirring overnight. The suspension was filtered and the solid residue (0.6 g) washed with acetone (10 mL) and triturated once again as described above to give (S)-methoxyphenylacetic acid salt of [1-(3-chloro-naphthalen-1-yl)-ethyl]amine (0.45 g). The solid was stirred in a mixture of aqueous std NaHCO$_3$ (20 mL) and DCM (20 mL). The organic phase washed with brine (20 mL), dried and concentrated in vacuo to give the title compound intermediate 2 (0.25 g) as a colourless oil. The mother liquors from the precipitation and first trituration were collected, concentrated in vacuo, treated with aqueous std NaHCO$_3$ (20 mL) and extracted with DCM (20 mL). The colourless oil thus obtained (1 g) was treated with (R)-methoxyphenylacetic acid (0.8 g) in acetone (8 mL) as described above (one precipitation and two triturations) to give (R)-methoxyphenylacetic acid salt of 1-(3-chloro-naphthalen-1-yl)-ethylamine (0.43 g). A portion of this solid (200 mg) was stirred in a mixture of aqueous std NaHCO$_3$ (10 mL) and DCM (10 mL). The organic phase washed with brine (20 mL), dried and concentrated in vacuo to give the title compound intermediate 3 (0.100 g) as colourless oil.

Intermediate 2 (Enantiomer 2):

NMR (d$_6$-DMSO): δ (ppm) 8.14 (dd, 1H); 7.94-7.85 (m, 2H); 7.73 (d, 1H); 7.58-7.50 (m, 2H); 4.80 (q, 1H); 1.35 (d, 3H).

MS (ES/+): m/z=189 [M-NH$_2$]$^+$. [α]$_D$=+69.7 (c=0.96, CH$_3$CN)

SFC (Gilson) analytical conditions: column: Chiralcel OD 25×4.6 mm; mobile phase: CO$_2$/Ethanol+0.1% Isopropanol 92/8 v/v; flow rate=2.5 mL/min; P=180 bar; T=35° C.; detection: λ=225 nm): retention time=13.8 minutes; purity (a/a %)>99%.

Intermediate 3 (Enantiomer 1):

NMR (d$_6$-DMSO): δ (ppm) 8.14 (dd, 1H); 7.94-7.85 (m, 2H); 7.73 (d, 1H); 7.58-7.50 (m, 2H); 4.80 (q, 1H); 1.35 (d, 3H).

MS (ES/+): m/z=189 [M-NH$_2$]$^+$. [α]$_D$=−66.9 (c=1.065, CH$_3$CN)

SFC (Gilson) analytical conditions: column: Chiralcel OD 25×4.6 mm; mobile phase: CO$_2$/Ethanol+0.1% Isopropanol 92/8 v/v; flow rate=2.5 mL/min; P=180 bar; T=35° C.; detection: λ=225 nm): retention time=12.4 minutes; purity (a/a %)>99%.

Intermediate 4

[1-(3,5-Dichlorophenyl)ethyl]amine

A solution of 3,5-dichlorobenzaldehyde (54.3 g) in dry THF (300 mL) was added dropwise to lithium bis(trimethylsilyl)-amide (1M solution in THF −340 mL) at −30° C. under a Nitrogen atmosphere. The resulting orange mixture was allowed to warm to −5° C. under stirring in a Nitrogen atmosphere in 1 hour, then it was cooled down to −60° C. and methyllithium (1.6M solution in Et2O −290 mL) was added keeping the internal temperature of the reaction mixture <−55° C.

The resulting dark violet reaction mixture was stirred for 1 hour at −60° C. under a Nitrogen atmosphere, then it was carefully quenched at −60° C. with 2N hydrochloric acid solution (20 mL) followed by 6N hydrochloric acid solution to pH=2. The reaction mixture was concentrated in vacuo and the aqueous residue washed with 1:1 CH/Et2O (500 mL). The separated aqueous phase was then made basic (pH=14) at 0° C. with NaOH pellets. The basic aqueous phase was extracted with Et2O (4×400 mL), the collected organic layers were dried and concentrated in vacuo to give the title compound (60 g) as a yellow oil.

T.l.c.: DCM/MeOH 9:1, Rf=0.5 (detection with ninhydrine).

NMR (CDCl$_3$): δ (ppm) 7.25-7.15 (m, 3H); 4.05 (q, 1H); 1.35 (d, 3H).

MS (ES/+): m/z=190 [M+H]$^+$.

Intermediate 5 and Intermediate 6

[1-(3,5-Dichlorophenyl)ethyl]amine (enantiomer 1) and [1-(3,5-dichlorophenyl)ethyl]amine (enantiomer 2)

A solution of (S)-methoxyphenylacetic acid (23 g) in acetone (140 mL) was added to a solution of intermediate 4 (25 g) in acetone (140 mL). The thick suspension was heated at 56° C. for 1 hour then it was stirred at r.t. overnight. The slurry was filtered and the solid residue washed with acetone (200 mL). The solid (47 g) was triturated in acetone (500 mL) by heating to reflux for 1 hour, cooling to r.t. and stirring overnight. The suspension was filtered and the solid residue (29 g) washed with acetone (500 mL) and triturated three times as described above to give (S)-methoxyphenylacetic acid salt of [1-(3,5-dichloro-phenyl)-ethyl]amine (16.6 g). The solid was stirred in a mixture of saturated sodium hydrogen carbonate solution (200 mL) and DCM (200 mL). The organic phase was separated, washed with brine (200 mL), dried and concentrated in vacuo to give the title compound intermediate 5 (8.2 g) as a colourless oil.

The same procedure was performed on a distinct batch of intermediate 4 (7.5 g) to obtain the title compound intermediate 5 (1.6 g); the mother liquors from the precipitation were evaporated in vacuo to give a residue (9.5 g), which was treated with saturated sodium hydrogen carbonate solution (50 mL) and extracted with DCM (50 mL). The colourless oil thus obtained (5 g) was treated with (R)-methoxyphenylacetic acid (4.3 g) in acetone as described above (one precipitation and two triturations) to give (R)-methoxyphenylacetic acid salt of [1-(3,5-dichloro-phenyl)-ethyl]amine (3.26 g). The solid was stirred in a mixture of saturated sodium hydrogen carbonate solution (50 mL) and DCM (50 mL). The organic phase washed with brine (50 mL), dried and concentrated in vacuo to give the title compound intermediate 6 (1.6 g) as colourless oil.

Intermediate 5: (Enantiomer 1)

NMR (CDCl$_3$): δ (ppm) 7.25-7.15 (m, 3H); 4.05 (q, 1H); 1.35 (d, 3H).

MS (ES/+): m/z=190 [M+H]$^+$.

HPLC (column: Chiral-AGP 15 cm×2 mm, 5 µm; injection volume=1 µL; mobile phase: ammonium phosphate buffer 100 mM pH=4.4/MeOH isocratic 99/1% v/v; flow rate=0.13 mL/min; detection: %=210 nm): retention time=5.4 minutes; purity (a/a %)>98%.

Intermediate 6: (Enantiomer 2)

NMR (CDCl$_3$): δ (ppm) 7.25-7.15 (m, 3H); 4.05 (q, 1H); 1.35 (d, 3H).

MS (ES/+): m/z=190 [M+H]$^+$.

HPLC (column: Chiral-AGP 15 cm×2 mm, 5 µm; injection volume=1 µL; mobile phase: ammonium phosphate buffer 100 mM pH=4.4/MeOH isocratic 99/1% v/v; flow rate=0.13 mL/min; detection: λ=210 nm): retention time=6.2 minutes; purity (a/a %)>99%.

Intermediate 7

1-(3-Chloro-1-naphthalenyl)methanamine

The 3-chloro-1-naphthalenecarbaldehyde (2 g) dissolved in dry THF (12 mL) was added dropwise to lithium bis(trimethylsilyl)amide 1M in THF (11.5 mL) previously cooled at −40° C. The resulting yellow mixture was stirred from −40° C. to −20° C. over 1.5 h; then it was cooled down at −50° C. and lithium aluminium hydride 1M in Et2O (10.6 mL) was added; the mixture was stirred at −40° C. for 2 h then it was quenched with HCl 2N (10 mL) and allowed to reach room temperature. The reaction mixture was diluted with further aqueous HCl 2N solution (20 mL) and extracted with CH/Et$_2$O 1/1 (50 mL). The acidic aqueous phase was basified at 0° C. with NaOH pellets until pH=14, then it was extracted with diethyl ether (2×150 mL). The organic phase was dried and concentrated in vacuo to give the title compound (1.78 g) as a white solid.

T.l.c.: DCM/MeOH 8:2, Rf=0.43 (detection with ninhydrine).

MS (ES/+): m/z=175 [M−NH$_2$]$^+$.

Intermediate 8

[2,2-Bis(methyloxy)ethyl][1-(3-chloro-1-naphthalenyl)ethyl]amine (Enantiomer 2)

A mixture of intermediate 2 (80 mg), 2-bromo-1,1-bis (methyloxy)ethane (92 µL) and K$_2$CO$_3$ (107.5 mg) in anhydrous DMF (2 ml) was processed by microwave irradiation at 150° C. for 10 min (3 cycles). Additional 2-bromo-1,1-bis (methyloxy)ethane (23 µL) was added to the mixture which was processed by microwave irradiation at 150° C. for 10 min (1 cycle). The mixture was allowed to cool to rt, water was added and mixture extracted three times with AcOEt, the organic phases collected, washed with brine, dried and evaporated under vacuum to give a crude which was purified by flash cromathography eluting with CH:AcOEt=9:1 to 85:15 to afford the title compound (114 mg) as a colourless oil.

T.l.c.: CH/AcOEt 7:3, Rf=0.26 (detection with ninhydrine).

MS (ES/+): m/z=294 [M+H]$^+$.

Intermediate 9

N-[(3-chloro-1-naphthalenyl)methyl]-2,2-bis(methyloxy)ethanamine

A mixture of intermediate 7 (100 mg), 2-bromo-1,1-bis (methyloxy)ethane (74 µL) and K$_2$CO$_3$ (108 mg) in anhydrous DMF (2 ml) was processed by microwave irradiation at 150° C. for 10 min. The mixture was allowed to cool to rt, water was added and mixture extracted with AcOEt, the organic phases collected, washed with brine, dried and evaporated under vacuum to give a crude which was purified by flash cromathography eluting with CH:AcOEt=10:0 to 9:1 to afford the title compound (127 mg) as a colourless oil.

NMR (CDCl3): δ (ppm) 8.03 (dd, 1H); 7.73 (dd, 1H); 7.71 (s, 1H); 7.49 (m, 2H); 7.45 (s, 1H); 4.49 (t, 1H); 4.22 (s, 2H); 3.36 (s, 6H); 2.83 (d, 2H).

Intermediate 10

[N-[(3,5-dichlorophenyl)methyl]-2,2-bis(methyloxy) ethanamine

A mixture of [(3,5-dichlorophenyl)methyl]amine (100 mg), 2-bromo-1, 1bis(methyloxy)ethane (123 µL) and K$_2$CO$_3$ (95 mg) in anhydrous DMF (2 mL) was processed by microwave irradiation at 150° C. for 10 min (3 cycles). The mixture was allowed to cool to rt, water was added and mixture extracted three times with AcOEt, the organic phases collected, washed with brine, dried and evaporated under vacuum to give a crude which was purified by flash cromathography eluting with CH:AcOEt=9:1 to 85:15 to afford the title compound (120 mg) as a colourless oil.

MS (ES/+): m/z=264 [M+H]$^+$.

Intermediate 11

N-[1-(3,5-dichlorophenyl)ethyl]-2,2-bis(methyloxy) ethanamine (Enantiomer 2)

A mixture of intermediate 6 (250 mg), 2-bromo-1,1-bis(methyloxy)ethane (218 µL) and $K_2CO_3$ (268 mg) in anhydrous DMF (2 mL) was processed by microwave irradiation at 150° C. for 10 min (3 cycles). The mixture was allowed to cool to rt, water was added and mixture extracted three times with AcOEt, the organic phases collected, washed with brine, dried and evaporated under vacuum to give a crude which was purified by flash cromathography eluting with CH:AcOEt=9:1 to 85:15 to afford the title compound (125 mg) as a colourless oil.

MS (ES/+): m/z=278 [M+H]$^+$.

Intermediate 12

N-[1-(3,5-dichlorophenyl)ethyl]-2,2-bis(methyloxy) ethanamine (Enantiomer 1)

A mixture of intermediate 5 (356 mg), 2-bromo-1,1-bis(methyloxy)ethane (338 µL) and $K_2CO_3$ (345 mg) in anhydrous DMF (2 mL) was processed by microwave irradiation at 150° C. for 10 min (3 cycles). The mixture was allowed to cool to rt, water was added and mixture extracted three times with AcOEt, the organic phases collected, washed with brine, dried and evaporated under vacuum to give a crude which was purified by flash cromathography eluting with CH:AcOEt=9:1 to 85:15 to afford the title compound (125 mg) as a colourless oil.

MS (ES/+): m/z=278 [M+H]$^+$.

Intermediate 13

4-(4-fluorophenyl)-4-isocyanato-1-methylpiperidine 4-(4-fluorophenyl)-1-methyl-4-piperidinecarboxylic acid hydrochloride (273 mg) was dissolved in dry toluene (10 mL) and, under a Nitrogen athmosphere and at r.t., TEA (0.33 mL) and diphenylphosphoryl azide (0.34 mL) were added. The mixture was refluxed for 4 h. Then water and AcOEt were added; the organic phase was separated and washed with brine, dried and evaporated under vacuum to give a crude which was purified by flash chromatography (elution with DCM:MeOH 9:1) to afford the title compound (47 mg) as white foam.

MS (ES/+): m/z=235 [M+H]$^+$.

Intermediate 14

N-[2,2-bis(methyloxy)ethyl]-N-[(3,5-dichlorophenyl)methyl]-N'-[4-(4-fluorophenyl)-1-methyl-4-piperidinyl]urea A solution of intermediate 13 (70 mg), and intermediate 10 (112 mg) in anhydrous THF (10 mL) was heated under a Nitrogen atmosphere at 60° C. for 4 h. The mixture was allowed to cool to rt, water was added and the mixture extracted three times with AcOEt, the organic phases collected, washed with brine, dried and evaporated under vacuum to give a crude which was purified by flash cromathography eluting with DCM:MeOH=97:3 to 95:5 to afford the title compound (86 mg) as a white foam.

MS (ES/+): m/z=498 [M+H]$^+$.

Intermediate 15

N-[2,2-Bis(methyloxy)ethyl]-N-[1-(3,5-dichlorophenyl)ethyl]-N'-[4-(4-fluorophenyl)-1-methyl-4-piperidinyl]urea (Enantiomer 1)

A solution of intermediate 13 (40 mg), and intermediate 12 (61.7 mg) in anhydrous THF (6 mL) was heated under a Nitrogen atmosphere at 60° C. for 3.5 h and at 70° C. for 1 h. Additional intermediate 12 (33 mg) in anhydrous THF (0.3 ml) was added to the mixture which was heated at 70° C. for further 7 h. In order to bring reaction to completion anhydrous toluene (5 mL) was added, THF removed by evaporation, intermediate 12 (47 mg) added and mixture refluxed for 14 h. The mixture was concentrated in vacuo and the residue purified by flash chromatography eluting with DCM:MeOH=97:3 to 95:5 to afford the title compound (42 mg) as a white foam.

T.l.c.: DCM/MeOH 95:5, Rf=0.11 (detection with ninhydrine).

MS (ES/+): m/z=512 [M+H]$^+$.

Following the same procedure described to obtain intermediate 15, intermediate 16 was prepared.

Intermediate 16

N-[2,2-Bis(methyloxy)ethyl]-N-[1-(3-chloro-1-naphthalenyl)ethyl]-N'-[4-(4-fluorophenyl)-1-methyl-4-piperidinyl]urea (Enantiomer 2)

Starting from intermediate 13 (38 mg) and intermediate 8 (142.6 mg), 47 mg of the title compound were obtained as a white foam.

MS (ES/+): m/z=528 [M+H]$^+$.

Intermediate 17

4-(4-fluorophenyl)-1-methyl-4-piperidinamine

TEA (1.3 mL) and diphenylphosphorylazide (0.98 mL) were added to a suspension of 4-(4-fluorophenyl)-1-methyl-4-piperidinecarboxylic acid hydrochloride (500 mg) in dry toluene (40 mL) under nitrogen atmosphere. The reaction mixture was heated at 90° C. and stirred overnight. Then it was cooled to rt and washed with an aqueous std $K_2CO_3$ solution. The aqueous layer was separated and the organic phase was dried and concentrated under vacuum to give a white solid. This material was suspended in HCl 5M (10 mL) and the reaction mixture was heated to reflux and stirred overnight. Then it was cooled to 0° C. and treated with aqueous 4M NaOH solution until pH=9. The aqueous layer was extracted with AcOEt, the combined organic extracts were washed with water and brine, dried and concentrated under vacuum to a residue which was purified by silica cartridge (from DCM to DCM/MeOH/TEA 90:5:5) to give the title compound (70 mg) as a white foam.

T.l.c.: DCM/MeOH/TEA 8:1:1, Rf=0.34 (detection with ninhydrine).

MS (ES/+): m/z=209 [M+H]$^+$.

Intermediate 18

N-(2-chloroethyl)-N'-[4-(4-fluorophenyl)-1-methyl-4-piperidinyl]urea

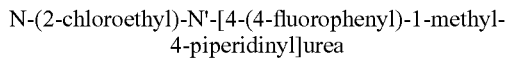

A solution of 1-chloro-2-isocyanatoethane (38 mg), and intermediate 17 (75 mg) in anhydrous THF (4 mL) was stirred under a Nitrogen atmosphere at rt for 8 h. Water and AcOEt were added, the organic phase separated, dried and evaporated under vacuum to give a crude which was purified by flash chromatography eluting with DCM:MeOH=97:3 to 95:5 to afford the title compound (92 mg) as a white foam.

T.l.c.: DCM/MeOH 9:1, Rf=0.45 (detection with ninhydrine).

MS (ES/+): m/z=314 [M+H]$^+$.

Intermediate 19

1-[4-(4-fluorophenyl)-1-methyl-4-piperidinyl]-2-imidazolidinone

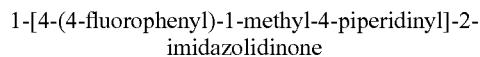

Intermediate 18 (92 mg) was dissolved in dry THF (5 mL) and, at 0° C. and under a Nitrogen athmosphere, NaH 60% dispersion in mineral oil (14 mg) was added. The mixture was allowed to warm to rt and stirred under these conditions for 8 h. Water and AcOEt were added; the organic phase separated and washed with brine, dried and evaporated under vacuum to give a crude which was purified by flash chromatography (elution with DCM-MeOH from 9:1 to 8:2) to afford the title compound (78 mg) as white foam.

MS (ES/+): m/z=278 [M+H]$^+$.

Intermediate 20

4-(Bromomethyl)-2-naphthalenecarbonitrile

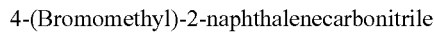

To a solution of 4-(hydroxymethyl)-2-naphthalenecarbonitrile (200 mg) in dry DCE (5 mL), CBr$_4$ (542.8 mg) and (Ph)$_3$P were added, the resulting mixture was stirred at r.t. for 40 min and then quenched with 40 mL of water. The aqueous phase washed with DCM (3×40 mL). The combined organic extracts were dried, concentrated, and purified by flash chromatography (CH/AcOEt from 8:2 to 1:1) to give the title compound (216 mg) as a white foam.

MS (ES/+): m/z=247 [M+H]$^+$.

Intermediate 21 and 22

Methyl 4-bromo-7-fluoro-2-naphthalenecarboxylate and methyl 4-bromo-6-fluoro-2-naphthalenecarboxylate

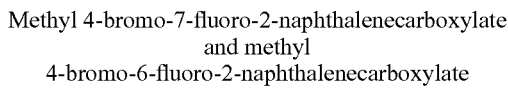

Isoamylnitrite (3.56 mL) dissolved in dimethoxyethane (18 mL) and a solution of 2-amino-4-fluorobenzoic acid (4.11 g) in dimethoxyethane (18 mL) were both added in separate streams at matching rate over 90 min to a refluxing solution of 3-bromo-coumalic acid methyl ester (3 g) in dimethoxyethane (25 mL) and catalytic amount of trifluoroacetic acid (21 mg). The reaction mixture was heated under reflux for a further 1 h after the end of the additions. Then the temperature was decreased to 50° C. and toluene (40 mL) was added. The mixture was then cooled to r.t., the phases were separated and the organic one was extracted with aqueous 0.5 M NaOH (20 mL), aqueous 5% sodium metabisolfite (20 mL), water (20 mL), aqueous 2M HCl (20 mL) and finally water (20 mL). Solvent was then removed by evaporation under reduced pressure to give a crude which was purified by Biotage Flash Chromatography eluting with CH:AcOEt=95:5 to give the title compound 21 (625 mg) and title compound 22 (547 mg) as yellow oils.

Intermediate 21

T.l.c.: CH/AcOEt 7:3, Rf=0.67.

NMR (CDCl$_3$): δ (ppm) 8.48 (s, 1H); 8.31 (s, 1H); 8.27 (dd, 1H); 7.56 (dd, 1H); 7.46 (td, 1H); 3.96 (s, 3H).

Intermediate 22

T.l.c.: CH/AcOEt 7:3, Rf=0.60.

NMR (CDCl$_3$): δ (ppm) 8.53 (s, 1H); 8.36 (s, 1H); 7.94 (dd, 1H); 7.88 (d, 1H); 7.34 (td, 1H); 3.96 (s, 3H).

Intermediate 23

4-Bromo-7-fluoro-2-naphthalenecarboxylic Acid

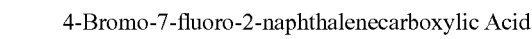

Intermediate 21 (970 mg) was dissolved in THF (20 mL) and water (10 mL) and then LiOH.H$_2$O (577 mg) was added. The mixture was heated at 80° C. for 2 h. Then it was cooled to r.t. and aqueous 2M HCl solution was added. The aqueous phase was extracted with AcOEt and the organic extracts were dried and evaporated in vacuo to give the title compound (850 mg) as a yellow solid.

NMR (d$_6$-DMSO): δ (ppm) 13.4 (bs, 1H); 8.63 (s, 1H); 8.23 (dd, 1H); 8.18 (s, 1H); 8.07 (dd, 1H); 7.71 (td, 1H).

Intermediate 24

4-bromo-6-fluoro-2-naphthalenecarboxylic acid

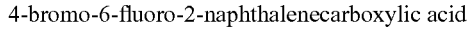

Intermediate 22 (3.89 g) was dissolved in THF (60 mL) and water (30 mL) and then LiOH.H$_2$O (2.32 g) was added. The mixture was heated at 80° C. for 2 h. Then it was cooled to r.t. and aqueous 2M HCl solution was added. The aqueous phase was extracted with AcOEt and the organic extracts were dried and evaporated in vacuo to give the title compound (3.4 g) as a yellow solid.

HPLC(LC/MS): t$_R$=4.00 min

MS (ES/−): m/z=267 [M−H]$^−$

Intermediate 25

4-Bromo-7-fluoro-N-hydroxy-2-naphthalenecarboxamide

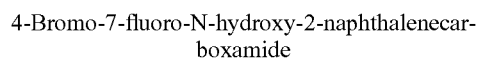

Intermediate 23 (850 mg) was dissolved in DMF (3 mL) and then TBTU (1.32 g) and DIPEA (1.9 mL) were added. The mixture was stirred for 30 min under a Nitrogen atmophere and then hydroxylamine hydrochloride (286 mg) was added; after stirring for 2 h aqueous std NH$_4$Cl solution was added and the aqueous phase was extracted with AcOEt. The organic phase was then washed with aqueous std NaHCO$_3$ solution, dried and evaporated in vacuo to give a crude which was triturated with pentane to afford the title compound (360 mg) as a withish solid.

MS (ES/+): m/z=284 [M+H]$^+$.

Intermediate 26

4-Bromo-7-fluoro-2-naphthalenecarbonitrile

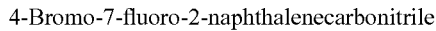

Intermediate 25 (360 mg) was suspended in fluoro benzene (11 mL) under Nitrogen atmosphere at r.t. and phosphorous tribromide (358 □L) was dropped on the mixture over 5 min. The suspension was refluxed at 80° C. for 18 h; then it was cooled to r.t. and aqueous std NaHCO$_3$ solution was added and the aqueous phase extracted with AcOEt. The organic extracts were collected, dried and evaporated in vacuo to give a crude which was purified by biotage flash cromathography eluting with CH:AcOEt=98:2 to afford the title compound (200 mg) as a pale brown solid.

NMR (d$_6$-DMSO): δ (ppm) 8.66 (s, 1H); 8.32 (dd, 1H); 8.28 (d, 1H); 8.01 (dd, 1H); 7.84 (dt, 1H).

Intermediate 27

4-Bromo-6-fluoro-2-naphthalenecarbonitrile

A solution of intermediate 24 (3.2 g), TBTU (4.58 g) and DIPEA (3.19 mL) in anhydrous DMF (50 ml) was stirred at r.t. for 1 h under a Nitrogen atmosphere. 1,1,1,3,3,3-Hexamethyldisilazane (5.02 mL) was added and the mixture stirred at r.t. overnight. The mixture washed with aqueous 5% NaHCO$_3$ solution, with an aqueous 2M HCl solution, and then the organic layer was dried, concentrated in vacuo to obtain a compound intermediate (3.15 g) which was dissolved in thionyl chloride (45 mL) and refluxed for 2 h under a Nitrogen athmosphere. Then the solvent was removed in vacuo to obtain the title compound as a pale brown solid (1.66 g).

NMR (CDCl$_3$): δ (ppm) 8.18 (s, 1H); 7.94 (d, 1H); 7.93 (s, 1H); 7.91 (d, 1H); 7.43 (td, 1H).

Intermediate 28

4-Ethenyl-7-fluoro-2-naphthalenecarbonitrile

A solution of intermediate 26 (25 mg), TETRAKIS (triphenylphosphine) Palladium (0) (5 mg), tributyl(ethenyl)stannane (32 □L) and one crystal of hydroquinone in dry toluene (1 mL) was heated at 110° C. for 4 h. The mixture was then cooled to r.t. and aqueous std NaHCO$_3$ solution and AcOEt were added; the organic phase was separated, washed with aqueous 10% KF solution, dried and evaporated in vacuo to give the crude. It was then purified by flash cromatography eluting by CH:AcOEt=9:1, to give the title compound (14 mg) as a yellow solid.

NMR (d$_6$-DMSO): δ (ppm) 8.51 (s, 1H); 8.40 (dd, 1H); 7.98 (d, 1H); 7.92 (dd, 1H); 7.70 (td, 1H); 7.57 (dd, 3H); 6.07 (d, 1H); 5.65 (d, 1H).

Intermediate 29

4-Ethenyl-6-fluoro-2-naphthalenecarbonitrile

A solution of intermediate 27 (1.66 g), TETRAKIS (triphenylphosphine) Palladium (0) (485 mg), tributyl(ethenyl)stannane (2.34 mL) and one crystal of hydroquinone in dry toluene (50 mL) was heated at 110° C. for 4 h. The mixture was then cooled to r.t. and aqueous std NaHCO$_3$ solution and AcOEt were added; the organic phase was separated, washed with aqueous 10% KF solution, dried and evaporated in vacuo to give the crude. It was then purified by flash chromatography eluting by CH:AcOEt=95:5 to 9:1, to give the title compound (1.21 g) as a yellow solid.

T.l.c.: CH/AcOEt 95:5, Rf=0.39.

NMR (CDCl$_3$): δ (ppm) 8.13 (s, 1H); 7.91 (dd, 1H); 7.72 (dd, 1H); 7.71 (s, 1H); 7.38 (td, 1H); 7.25 (dd, 1H); 5.83 (d, 1H); 5.61 (d, 1H).

Intermediate 30

7-Fluoro-4-formyl-2-naphthalenecarbonitrile

Intermediate 28 (14 mg) was dissolved in THF (1.5 mL) and water (0.3 mL); aqueous 4% osmium tetroxide solution (22 □L) and sodium periodate (30 mg) were added and the solution was vigorously stirred at r.t. and under Nitrogen atmosphere for 4 h. Then a 5% solution of sodium methabisolfite in aqueous std NaHCO$_3$ solution was added; the organic phase was extracted with AcOEt, dried and evaporated in vacuo to give the title compound (14 mg) as a pale yellow solid.

NMR (d$_6$-DMSO): δ (ppm) 10.38 (s, 1H); 9.23 (dd, 1H); 8.90 (s, 1H); 8.50 (s, 1H); 8.03 (dd, 1H); 7.87 (td, 1H).

Intermediate 31

6-Fluoro-4-formyl-2-naphthalenecarbonitrile

Intermediate 29 (100 mg) was dissolved in THF (3 mL) and water (1 mL); aqueous 4% osmium tetroxide solution (310 □L) and sodium periodate (217 mg) were added and the solution was vigorously stirred at r.t. and under Nitrogen atmosphere for 4 h. Then a 5% solution of sodium methabisolfite in aqueous std NaHCO$_3$ solution was added; the organic phase was extracted with AcOEt, dried and evaporated in vacuo to give the title compound (99 mg) as a pale yellow solid.

NMR (CDCl$_3$): δ (ppm) 10.31 (s, 1H); 9.00 (dd, 1H); 8.44 (s, 1H); 8.14 (s, 1H); 8.01 (dd, 1H); 7.50 (td, 1H).

Intermediate 32

4-(Bromomethyl)-7-fluoro-2-naphthalenecarbonitrile

Intermediate 30 (540 mg) was dissolved in MeOH (30 mL) under a Nitrogen athmosphere, the solution was cooled at 0° C. and NaBH$_4$ (102 mg) was added portionwise. After 1 h, aqueous NH4Cl std solution was added and the solution was stirred for ½ h. Then AcOEt was additioned and the organic phase was separated, dried and concentrated in vacuo to give a crude which was purified by flash chromatography by CH:AcOEt=9:1 to afford the a compound intermediate {MS (ES/+): m/z=202 [M+H]$^+$} (383 mg) as a white solid.

A portion of this compound (200 mg) was suspended in DCE (10 mL) at r.t. and under a Nitrogen athmosphere; then triphenylphosphine (524 mg) and carbontetrabromide (498 mg) were added and the solution was stirred under these conditions for 2 h. Water was added and the aquoeus phase was extracted with DCM. The organic extracts were dried and evaporated in vacuo to give a crude which was purified by flash chromatography eluting with CH:AcOEt=99:1 to 9:1 to afford the title compound (130 mg) as a white solid.

NMR (CDCl$_3$): δ (ppm) 8.2 (dd, 1H); 8.15 (s, 1H); 7.63 (s, 1H); 7.56 (dd, 1H); 7.53 (td, 1H); 4.86 (s, 2H).

Intermediate 33

4-(Bromomethyl)-6-fluoro-2-naphthalenecarbonitrile

Intermediate 31 (8300 mg) was dissolved in MeOH (50 mL) under a Nitrogen athmosphere, the solution was cooled at 0° C. and NaBH$_4$ (158 mg) was added portionwise. After 1 h, aqueous NH4Cl std solution was added and the solution was stirred for ½ h. Then AcOEt was additioned and the organic phase was separated, dried and concentrated in vacuo to give a crude which was purified by flash chromatography by CH:AcOEt=9:1 to afford the a compound intermediate {MS (ES/+): m/z=202 [M+H]$^+$} (383 mg) as a white solid.

A portion of this compound (180 mg) was suspended in DCE at r.t. and under a Nitrogen athmosphere; then triphenylphosphine (473 mg) and carbontetrabromide (450 mg) were added and the solution was stirred under these conditions for 2 h. Water was added and the aquoeus phase was extracted with DCM. The organic extracts were dried and evaporated in vacuo to give a crude which was purified by flash chromatography eluting with CH:AcOEt=99:1 to 9:1 to afford the title compound (124 mg) as a white solid.

NMR (CDCl$_3$): δ (ppm) 8.2 (s, 1H); 7.96 (dd, 1H); 7.78 (dd, 1H); 7.7 (s, 1H); 7.43 (td, 1H); 4.83 (s, 2H).

Example 1

1-[(3,5-dichlorophenyl)methyl]-3-[4-(4-fluorophenyl)-1-methyl-4-piperidinyl]-1,3-dihydro-2H-imidazol-2-one Intermediate 14 (86 mg) was dissolved in MeOH (2.5 mL) and aqueous 2M HCl solution (2.5 mL) was added. The mixture was heated at 60° C. for 0.5 h, then solvents were removed by evaporation under vacuum. DCM and aqueous 2N NaOH solution were added to the crude residue and the aqueous phase extracted with DCM. The organic extracts were collected, washed with brine, dried and evaporated under vacuum to give a crude which was purified by flash cromathography eluting with DCM:MeOH=9:1 to 80:20 to afford the title compound (75 mg) as a white solid.

NMR (-CDCl$_3$): δ (ppm) 7.31 (s, 1H); 7.29 (s, 2H); 7.23 (dd, 2H); 7.04 (m, 2H); 6.45 (2d, 1H); 6.28 (2d, 1H); 4.74 (s, 2H); 2.95 (bd, 4H); 2.5/2.3 (m, 4H); 2.4 (s, 3H). MS (ES/+): m/z=434 [M+H]$^+$.

Example 2

1-[(3,5-dichlorophenyl)methyl]-3-[4-(4-fluorophenyl)-1-methyl-4-piperidinyl]-1,3-dihydro-2H-imidazol-2-one hydrochloride Example 1 (150 mg) was dissolved in Et2O (10 mL), cooled to 0° C. and treated with HCl 1M solution in Et2O (0.42 mL). The mixture was stirred at 0° C. for 10 minutes, then it was concentrated in vacuo and the residue was triturated with pentane to give the title compound (148.0 mg) as a white solid.

NMR (d$_6$-DMSO): δ 12 (ppm) 9.8-9.6 (br, 1H); 7.41 (s, 1H); 7.34 (s, 2H); 7.20 (dd, 2H); 7.00 (m, 2H); 6.5 (2d, 1H); 6.20 (2d, 1H); 4.55 (s, 2H); 2.90 (bd, 4H); 2.5 (m, 4H); 2.4 (s, 3H).

Example 3

1-[(3,5-Dichlorophenyl)methyl]-3-[4-(4-fluorophenyl)-4-piperidinyl]-1,3-dihydro-2H-imidazol-2-one A mixture of example 2 (11 mg), 1-chloroethyl chloridocarbonate (4 μL) and TEA (6.5 μL) in anhydrous 1,2-dichloroethane (100 μL) was refluxed under a Nitrogen atmosphere for 1 h. Additional 1-chloroethyl chloridocarbonate (3×4 μL) and TEA (3×6.5 μL) were added during the following 5 h while stirring. The mixture was concentrated under vacuum, MeOH (200 μL) was added to the residue and resulting mixture refluxed for 1 h. DCM and an aqueous std NaHCO$_3$ solution were added to the crude residue and the aqueous phase extracted with DCM. The organic extracts were collected, dried and evaporated under vacuum to give a crude which was purified by flash cromathography (eluting with DCM:MeOH=95:5 to 9:1, then 8:2 containing 0.5% NH$_4$OH) to afford the title compound (5.8 mg) as a off-white foam.

T.l.c.: DCM/MeOH 8:2 containing 0.5% NH$_4$OH, Rf=0.45 (detection with ninhydrine).

MS (ES/+): m/z=420 [M+H]$^+$.
HPLC (walk-up): t$_R$=4.27 min.

Example 4

1-[1-(3,5-Dichlorophenyl)ethyl]-3-[4-(4-fluorophenyl)-1-methyl-4-piperidinyl]-1,3-dihydro-2H-imidazol-2-one (Enantiomer 1)

Intermediate 15 (42 mg) was dissolved in MeOH (1.4 mL) and aqueous 2M HCl solution (1.4 mL) was added. The mixture was heated at 60° C. for 2 h, then solvents removed by evaporation under vacuum. DCM and aqueous 2N NaOH solution were added to the crude residue and the aqueous phase extracted with DCM. The organic extracts were collected, washed with brine, dried and evaporated under vacuum to give a crude which was purified by flash cromathography eluting with DCM:MeOH=9:1 to 8:2 to afford the title compound (32 mg) as a white foam.

T.l.c.: DCM/MeOH 95:5, Rf=0.13 (detection with ninhydrine).

MS (ES/+): m/z=448 [M+H]$^+$.

Following the same procedure described to obtain example 4, example 5 was prepared.

Example 5

1-[1-(3-Chloro-1-naphthalenyl)ethyl]-3-[4-(4-fluorophenyl)-1-methyl-4-piperidinyl]-1,3-dihydro-2H-imidazol-2-one (Enantiomer 2)

Starting from intermediate 16 (47 mg), 38 mg of the title compound were obtained as a white foam.

MS (ES/+): m/z=464 [M+H]$^+$.

Example 6

1-[1-(3,5-Dichlorophenyl)ethyl]-3-[4-(4-fluorophenyl)-1-methyl-4-piperidinyl]-1,3-dihydro-2H-imidazol-2-one hydrochloride (Enantiomer 1)

Example 4 (32 mg) was dissolved in Et2O (1.4 mL), cooled to 0° C. and treated with HCl 1M solution in Et$_2$O (0.128 mL). The mixture was stirred at 0° C. for 10 minutes, then it was concentrated in vacuo and the residue was triturated with pentane to give the title compound (22 mg) as a white solid.

NMR (d$_6$-DMSO): δ (ppm) 9.98 (bs, 1H); 7.50 (bs, 1H); 7.19 (bs, 2H); 7.13 (t, 2H); 7.06 (m, 2H); 6.99 (d, 1H); 6.91 (d, 1H); 5.20 (q, 1H); 3.47 (bm, 2H); 3.14-2.85 (bm, 4H); 2.79 (s, 3H); 2.27 (m, 2H); 1.62 (d, 3H).

MS (ES/+): m/z=448 [M+H]$^+$.
HPLC (walk-up): t$_R$=4.39 min.

Following the same procedure described to obtain example 6, example 7 was prepared.

Example 7

1-[1-(3-Chloro-1-naphthalenyl)ethyl]-3-[4-(4-fluorophenyl)-1-methyl-4-piperidinyl]-1,3-dihydro-2H-imidazol-2-one hydrochloride (Enantiomer 2)

Starting from example 5 (38 mg), 32 mg of the title compound were obtained as a white solid.

NMR (d$_6$-DMSO): δ (ppm) 10.10 (bs, 1H); 8.09 (d, 1H); 8.02 (s, 1H); 7.94 (d, 1H); 7.59 (t, 1H); 7.51 (t, 1H); 7.40 (s, 1H); 7.09 (m, 2H); 7.03 (m, 2H); 6.83 (d, 1H); 6.79 (d, 1H); 5.95 (q, 1H); 3.48 (bm, 2H); 3.1-2.5 (bm, 4H); 2.75 (bs, 3H); 2.3 (bt, 2H); 1.72 (d, 3H).

MS (ES/+): m/z=464 [M+H]$^+$.

HPLC (walk-up): $t_R$=4.55 min

Example 8

1-[(3,5-dichlorophenyl)methyl]-3-[4-(4-fluorophenyl)-1-methyl-4-piperidinyl]-2-imidazolidinone Intermediate 19 (45 mg) was dissolved in dry DMF (5 mL) and, under a Nitrogen athmosphere and at 0° C., NaH 60% dispersion in mineral oil (8 mg) was added and the solution was stirred for 20 min. Then 1,3-dichloro-5-(chloromethyl) benzene was added (34 mg) and the solution was stirred at rt for 8 h. Water and AcOEt were added; the organic phase separated and washed with brine, dried and evaporated under vacuum to give a crude which was purified by flash chromatography (elution with DCM-MeOH from 9:1 to 8:2) to afford the title compound (12 mg) as white foam.

MS (ES/+): m/z=436 [M+H]$^+$.

NMR (-CDCl$_3$): δ (ppm) 7.4 (m, 2H); 7.29 (s, 1H); 7.15 (s, 2H); 7.04 (t, 2H); 4.30 (s, 2H); 3.1 (bd, 4H); 2.85 (bm, 2H); 2.70 (bm, 2H); 2.4 (t, 2H); 2.35 (s, 3H), 2.15 (bt, 2H).

Following the same procedure described to obtain example 8, example 9, 10, 11 and 12 were prepared.

Example 9

4-({3-[4-(4-fluorophenyl)-1-methyl-4-piperidinyl]-2-oxo-1-imidazolidinyl}methyl)-2-naphthalenecarbonitrile Starting from Intermediate 19 (50 mg) and intermediate 20 (44 mg), 32 mg of the title compound were obtained as a white solid.

NMR (CDCl$_3$): δ (ppm) 8.3 (d, 1H); 8.2 (s, 1H); 8.0 (dd, 1H); 7.7 (td, 1H); 7.7 (td, 1H); 7.5 (s, 1H); 7.4 (dd, 2H); 7.0 (t, 2H); 4.8 (s, 2H); 3.1 (s, 4H); 2.9 (b, 4H); 2.6 (b, 2H); 2.4 (s, 3H); 2.3 (b, 2H).

Example 10

7-fluoro-4-({3-[4-(4-fluorophenyl)-1-methyl-4-piperidinyl]-2-oxo-1-imidazolidinyl}methyl)-2-naphthalenecarbonitrile Starting from Intermediate 19 (30 mg) and intermediate 32 (26 mg), 32 mg of the title compound were obtained as a white solid.

NMR (CDCl3): δ (ppm) 8.3 (dd, 1H); 8.2 (s, 1H); 7.6 (dtd, 1H); 7.5 (m, 1H); 7.5 (s, 1H); 7.4 (dd, 2H); 7.0 (t, 2H); 4.8 (s, 2H); 3.1 (s, 4H); 2.9 (b, 4H); 2.6 (b, 2H); 2.4 (s, 3H); 2.3 (b, 2H).

Example 11

6-fluoro-4-({3-[4-(4-fluorophenyl)-1-methyl-4-piperidinyl]-2-oxo-1-imidazolidinyl}methyl)-2-naphthalenecarbonitrile Starting from Intermediate 19 (30 mg) and intermediate 33 (26 mg), 32 mg of the title compound were obtained as a white solid.

NMR (CDCl3): δ (ppm) 8.3 (dd, 1H); 8.2 (s, 1H); 8.0 (dd, 1H); 8.0 (dd, 1H); 7.5 (s, 1H); 7.5 (dd, 1H); 7.0 (t, 2H); 4.8 (s, 2H); 3.1 (s, 4H); 2.8-3.0 (b, 4H); 2.2 (b, 2H); 2.4 (s, 3H); 2.2 (b, 2H).

Example 12

1-[(3-chloro-1-naphthalenyl)methyl]-3-[4-(4-fluorophenyl)-1-methyl-4-piperidinyl]-1,3-dihydro-2H-imidazol-2-one A solution of intermediate 9 (40 mg) and intermediate 13 (33, 5 mg) in anhydrous THF (3 mL) was processed by microwave irradiation at 150° C. for 10 min (2 cycles). The solvent was removed under vacuum to give a crude which was purified by a Mass Directed Preparative Instrument by Waters (System Fraction Lynx™) performed on a X Terra Prep MS C18 (30×150 mm; 10 μm) (mobile phase: from 99% [water+ 0.1% HCO$_2$H] and 1% [CH$_3$CN +0.1% HCO$_2$H] to 100% [CH$_3$CN +0.1% HCO$_2$H] in 8 min and 30"; 100% [CH$_3$CN +0.1% HCO$_2$H] for 6 min; from 100% [CH$_3$CN +0.1% HCO$_2$H] to 99% [water+0.1% HCO$_2$H] and 1% [CH$_3$CN +0.1% HCO$_2$H] in 30"; 99% [water+0.1% HCO$_2$H] and 1% [CH$_3$CN +0.1% HCO$_2$H] for 12"); T=rt; flow rate=40 mL/min; UV Detection: 210-400 nm; MS Detection Mode: ES (+)/ES (−), Mass Range: 100-900] to afford a compound intermediate (22 mg) as a colourless oil.

This intermediate was dissolved in MeOH (1.5 mL) and aqueous 2M HCl solution (1.5 mL) was added. The mixture was heated at 60° C. for 0.5 h, then solvents were removed by evaporation under vacuum. The crude obtained was coevaporated with Et2O and CH3CN to afford a compound (21 mg) a portion of which (15 mg) was dissolved in DCM (2 mL). Then aqueous std 2M K$_2$CO$_3$ solution (1.5 mL) was added and from separation of phases and evaporation of organic solvent the title compound (11 mg) was obtained as a white solid.

NMR (CDCl3): δ (ppm) 7.94 (d, 1H); 7.80 (m, 1H); 7.77 (d, 1H); 7.52 (t, 1H); 7.43 (t, 1H); 7.24 (m, 1H); 7.14 (dd, 2H); 6.95 (t, 2H); 6.35 (d, 1H); 6.12 (d, 1H). 5.14 (m, 2H); 2.94 (m, 2H); 2.76 (m, 2H); 2.28 (m, 4H); 2.28 (m, 3H).

The invention claimed is:

1. A compound of formula (I)

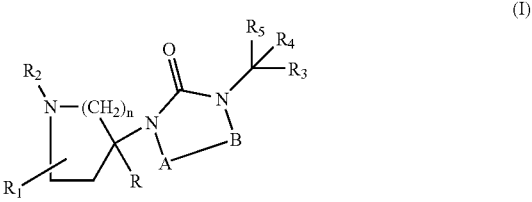

(I)

wherein:

R is a group selected from:

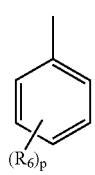

i)

ii)
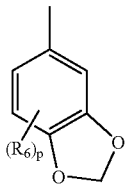

iii)
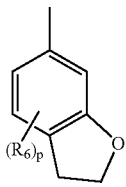
or iv)
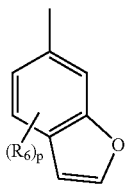

wherein $R_6$ is halogen, cyano, $C_{1-4}$ alkyl or trifluoromethyl and p is 2 or 3 or
$R_6$ is halogen, cyano, $C_{1-4}$ alkyl, $C_{1-4}$ alkoxy, trifluoromethoxy or trifluoromethyl and p is 0 or 1;
R1 is hydrogen;
$R_2$ is hydrogen or $(CH_2)_q R_7$;
$R_3$ and $R_4$ each independently are hydrogen or $C_{1-4}$ alkyl;
$R_5$ is selected from:
  phenyl substituted by 1 to 3 groups independently selected from trifluoromethyl, $C_{1-4}$ alkyl, cyano, $C_{1-4}$ alkoxy, trifluoromethoxy, halogen, $S(O)_r C_{1-4}$ alkyl or a phenyl substituted by a 5 or 6 membered heteroaryl group optionally substituted by 1 to 3 groups independently selected from trifluoromethyl, $C_{1-4}$ alkyl, cyano, $C_{1-4}$ alkoxy, trifluoromethoxy, halogen or $S(O)_r C_{1-4}$-alkyl;
  naphthyl substituted by 1 to 3 groups independently selected from trifluoromethyl, $C_{1-4}$ alkyl, cyano, $C_{1-4}$ alkoxy, trifluoromethoxy, halogen or $S(O)_r C_{1-4}$ alkyl;
  a 9 to 10 membered fused bicyclic heterocyclic group substituted by 1 to 3 groups independently selected from trifluoromethyl, $C_{1-4}$ alkyl, cyano, $C_{1-4}$ alkoxy, trifluoromethoxy, halogen or $S(O)_r C_{1-4}$ alkyl; or
  a 5 or 6 membered heteroaryl group substituted by 1 to 3 groups independently selected from trifluoromethyl, $C_{1-4}$ alkyl, cyano, $C_{1-4}$ alkoxy, trifluoromethoxy, halogen or $S(O)_r C_{1-4}$ alkyl;
$R_7$ is hydrogen, $C_{3-7}$ cycloalkyl, $C_{1-4}$ alkoxy, amine $C_{1-4}$ alkylamine, $(C_{1-4}$ alkyl$)_2$amine, $OC(O)NR_8R_9$ or $C(O)NR_8R_9$;
$R_8$ and $R_9$ each independently represent hydrogen, $C_{1-4}$alkyl or $C_{3-7}$ cycloalkyl;
A-B is a bivalent radical of formula (v), (vi) or (vii)

—CH=C($R_{11}$)— (v)

—C($R_{10}$)=CH— or (vi)

—C($R_{12}$)($R_{10}$)—C($R_{11}$)($R_{13}$)— (vii)

wherein $R_{10}$, $R_{11}$, $R_{12}$ and $R_{13}$ are hydrogen;

n is 1 or 2;
q is an integer from 1 to 4;
r is 1 or 2;
or a pharmaceutically acceptable salt thereof.

2. A compound as claimed in claim 1 wherein R is phenyl optionally substituted by one or two halogen or $C_{1-4}$ alkyl.

3. A compound as claimed in claim 2, wherein R is phenyl optionally substituted by one or two fluorine or methyl.

4. A compound as claimed in claim 1 wherein $R_5$ is phenyl optionally substituted by one or 2 groups selected from cyano, methyl, chlorine, bromine or fluorine, or $R_5$ is naphthyl optionally substituted by one group selected from cyano, methyl, chlorine, bromine or fluorine.

5. A compound as claimed in claim 1 wherein $R_2$ is hydrogen or $C_{1-4}$ alkyl.

6. A compound as claimed in claim 1 wherein $R_2$ is hydrogen or methyl.

7. A compound as claimed in claim 1 wherein $R_3$ is hydrogen and $R_4$ is hydrogen or methyl.

8. A compound as claimed in claim 1 wherein R is phenyl substituted by a fluorine, $R_1$ is hydrogen, $R_2$ is hydrogen or $C_{1-4}$ alkyl, $R_3$ is hydrogen, $R_4$ is hydrogen or methyl, $R_5$ is phenyl or naphthyl optionally substituted by one or two groups independently selected from cyano, chlorine, bromine or fluorine, $R_{10}$, $R_{11}$, $R_{12}$ or $R_{13}$ are hydrogen and n is 2.

9. A compound selected from
  1-[(3,5-dichlorophenyl)methyl]-3-[4-(4-fluorophenyl)-1-methyl-4-piperidinyl]-1,3-dihydro-2H-imidazol-2-one;
  1-[(3,5-dichlorophenyl)methyl]-3-[4-(4-fluorophenyl)-1-methyl-4-piperidinyl]-1,3-dihydro-2H-imidazol-2-one;
  1-[(3,5-Dichlorophenyl)methyl]-3-[4-(4-fluorophenyl)-4-piperidinyl]-1,3-dihydro-2H-imidazol-2-one,
  1-[1-(3,5-Dichlorophenyl)ethyl]-3-[4-(4-fluorophenyl)-1-methyl-4-piperidinyl]-1,3-dihydro-2H-imidazol-2-one;
  1-[1-(3-Chloro-1-naphthalenyl)ethyl]-3-[4-(4-fluorophenyl)-1-methyl-4-piperidinyl]-1,3-dihydro-2H-imidazol-2-one;
  1-[1-(3,5-Dichlorophenyl)ethyl]-3-[4-(4-fluorophenyl)-1-methyl-4-piperidinyl]-1,3-dihydro-2H-imidazol-2-one;
  1-[1-(3-Chloro-1-naphthalenyl)ethyl]-3-[4-(4-fluorophenyl)-1-methyl-4-piperidinyl]-1,3-dihydro-2H-imidazol-2-one;
  1-[(3,5-dichlorophenyl)methyl]-3-[4-(4-fluorophenyl)-1-methyl-4-piperidinyl]-2-imidazolidinone;
  4-({3-[4-(4-fluorophenyl)-1-methyl-4-piperidinyl]-2-oxo-1-imidazolidinyl}methyl)-2-naphthalenecarbonitrile;
  7-fluoro-4-({3-[4-(4-fluorophenyl)-1-methyl-4-piperidinyl]-2-oxo-1-imidazolidinyl}methyl)-2-naphthalenecarbonitrile;
  6-fluoro-4-({3-[4-(4-fluorophenyl)-1-methyl-4-piperidinyl]-2-oxo-1-imidazolidinyl}methyl)-2-naphthalenecarbonitrile;
  1-[(3-chloro-1-naphthalenyl)methyl]-3-[4-(4-fluorophenyl)-1-methyl-4-piperidinyl]-1,3-dihydro-2H-imidazol-2-one,
and enantiomers, diastereoisomers, and phamaceutically acceptable salts thereof.

10. A pharmaceutical composition comprising a compound as claimed in claim 1 in admixture with one or more pharmaceutically acceptable carriers or excipients.

* * * * *